(12) United States Patent
Spinelli et al.

(10) Patent No.: US 9,415,220 B1
(45) Date of Patent: Aug. 16, 2016

(54) AURICULAR STIMULATION FOR INFLAMMATORY PARASYMPATHETIC DISEASES

(71) Applicants: Julio César Spinelli, Bradenton, FL (US); Marco Peresini, Buenos Aires (AR)

(72) Inventors: Julio César Spinelli, Bradenton, FL (US); Marco Peresini, Buenos Aires (AR)

(73) Assignee: Synchromax, Inc., Lakewood Ranch, FL (US)

(*) Notice: Subject to any disclaimer, the term of this patent is extended or adjusted under 35 U.S.C. 154(b) by 0 days.

(21) Appl. No.: 13/956,065

(22) Filed: Jul. 31, 2013

Related U.S. Application Data

(60) Provisional application No. 61/677,846, filed on Jul. 31, 2012.

(51) Int. Cl.
*A61N 1/04* (2006.01)
*A61N 1/36* (2006.01)

(52) U.S. Cl.
CPC ........ *A61N 1/36032* (2013.01); *A61N 1/36139* (2013.01); *A61N 1/36053* (2013.01); *A61N 1/36114* (2013.01); *A61N 1/36117* (2013.01)

(58) Field of Classification Search
CPC ........... A61N 1/36032; A61N 1/36053; A61N 1/36114; A61N 1/36117; A61N 1/36139
USPC ................ 607/2, 44, 115, 116, 118, 136, 137
See application file for complete search history.

(56) References Cited

U.S. PATENT DOCUMENTS

| | | | |
|---|---|---|---|
| 7,471,800 B2 | 12/2008 | Neilson | |
| 8,412,100 B2 | 4/2013 | Sanguino et al. | |
| 8,554,321 B2 | 10/2013 | Ding et al. | |
| 2004/0034394 A1* | 2/2004 | Woods et al. | 607/46 |
| 2005/0033384 A1* | 2/2005 | Sacha | 607/57 |
| 2005/0165460 A1* | 7/2005 | Erfan | 607/57 |
| 2005/0201578 A1* | 9/2005 | Fischer | 381/315 |
| 2006/0064139 A1* | 3/2006 | Chung et al. | 607/45 |
| 2006/0122675 A1* | 6/2006 | Libbus et al. | 607/116 |
| 2008/0146892 A1* | 6/2008 | LeBoeuf et al. | 600/300 |
| 2008/0234779 A1* | 9/2008 | Pedersen et al. | 607/44 |
| 2008/0288016 A1* | 11/2008 | Amurthur et al. | 607/44 |
| 2011/0307030 A1* | 12/2011 | John | 607/45 |

OTHER PUBLICATIONS

Nuran Bradley, "Master of Science in Applied Mathematics & Computer Science," Department of Mathematical Sciences, Indiana University of South Bend, E-mail Address: nbradley@iusb.edu.

* cited by examiner

*Primary Examiner* — Christopher D Koharski
*Assistant Examiner* — Pamela M Bays
(74) *Attorney, Agent, or Firm* — Patrick J. S. Inouye; Leonid Kisselev

(57) ABSTRACT

Device, systems, methods and kits can be useful for auricular stimulation. One such device relates to auricular stimulation. The device includes an earpiece having an electrode arrangement configured and arranged to deliver a series of electrical stimulation signals to an auricular location. A pulse-generator circuit is configured and arranged to generate the series of electrical stimulation signals having a stimulation profile, and to deliver the electrical stimulation signals to the electrode arrangement. A sensor is configured and arranged to generate a feedback signal that is responsive to the electrical stimulation signals. A feedback circuit is configured and arranged to modify the stimulation profile in response to the feedback signal.

9 Claims, 20 Drawing Sheets

AURICULAR STIMULATION FOR INFLAMMATORY PARASYMPATHETIC DISEASES

OVERVIEW

Various therapeutic solutions can be obtained from modifying the inflammatory effect and its participation in many disease processes. In many instances, decreasing and/or slowing down the inflammatory process can be particularly useful for treatment of such disease processes. For instance, inflammation and hypertension may share some pathophysiological mechanisms, and therefore the treatment of one of the two conditions could have some impact on the other. It is believed that vagus nerve stimulation can decrease inflammation by suppressing cytokine production. Accordingly, vagus nerve stimulation can be particularly useful for therapies relating to diseases linked to inflammatory processes.

The vagus nerve is also associated with different brain regions. Thus, auricular stimulation is believed to be applicable for reduction or/and even elimination of some cases of Tinnitus (a constant buzzing-like sound in the ear), some anxiety disorders, obesity, depression, heart failure and heart failure progression, post infarct myocardial damage and post infarct myocardial damage prevention, obesity, migraines, Alzheimer's disease, fibromyalgia and arthritis.

The vagus nerve can also be stimulated in order to influence the complex neural network that affects the intra-beat and beat to beat control of the functioning of the heart. Vagal stimulation before, during and after occlusion/reperfusion of the coronary system, has been experimentally shown to reduce damage that occurs in the heart with an infarct and its associated mortality.

Other aspects of the present disclosure recognize that during ischemia and heart failure, afferent outputs from the heart's local neural system can overwhelm the system, causing it to malfunction by saturating and/or overloading the control system creating an overreaction in terms of sympathetic stimulation without its natural parasympathetic balance. It is believed that auricular stimulation can not only help restore that balance, but also slow down and even stop the excessive apoptosis rate that is triggered during the ischemia reperfusion cycle leading to reductions in the percentage of tissue that is destroyed by the infarct, experimentally up to 90% reductions in infarct size have been observed. The balancing effect of auricular nerve stimulation of the vagal system can be especially valuable in periods of ischemia and during the imbalances in autonomic control created by acute and chronic heart failure. It is believed that these mechanisms can contribute to a significantly reduced ischemic damage of the heart by tempering the over-reaction of the control system due to the overload of its afferent circuits and lead to a lower overall mortality rate. Auricular stimulation of the vagal system can also be used to reduce the maladaptive processes by providing balance to the control system. For instance, reperfusion by coronary angioplasty/stenting can reduce an excessive rate of apoptosis that can occur in the progression of heart failure or during an infarct. In certain instances, this action may start to occur at levels of stimulation that may not be sufficient or even unable to produce heart rate, pressure or other systemic level changes, since the action will be directly over the control system of the heart. This system can act even during the cardiac cycle and its actions will not manifest until a certain threshold is crossed. This does not mean that the therapeutic threshold is not below that level. Auricular stimulation is not only a minimally invasive way to stimulate the vagal system, but also enables the operator to stimulate both sides of the system (right and left) in a minimally invasive way; thereby facilitating treatment of a significant portion of the neural system that controls the heart.

Using auricular stimulation to activate the neural network that controls the heart can be used as an independent mechanism (in the context of a process and/or treatment) for inflammatory prevention, to explain the beneficial effects that have been seen over the progression of heart disease, and to prevent of myocardial infarction damage.

SUMMARY

Aspects of the present disclosure are directed toward auricular nerve stimulation at terminals in one and/or both ear lobes, and based on events that are simultaneous, synchronous, in alternating sequences and/or with different off times, and to providing systems, apparatuses, and methods for application of stimulation for reproducible stimulation of the auricular nerve or nerves with minimal operator dependence.

Device, systems, methods and kits can be useful for auricular stimulation. One such device relates to auricular stimulation. The device includes one or two earpieces having an electrode arrangement configured and arranged to deliver a series of electrical stimulation signals to one or two auricular locations. One or two pulse-generator circuits is/are configured and arranged to generate the series of electrical stimulation signals having a stimulation profile, and deliver the electrical stimulation signals to the electrode arrangement. A sensor is configured and arranged to generate a feedback signal that is responsive to the electrical stimulation signals. A feedback circuit is configured and arranged to modify the stimulation profile in response to the feedback signal.

Certain embodiments of the present disclosure are directed toward an auricular stimulation device that has an earpiece having an electrode and configured and arranged to deliver a series of electrical stimulation signals to a first auricular location of a particular individual based upon anatomical measurements from the particular individual. A pulse-generator circuit is configured and arranged to generate the series of electrical stimulation signals, and to deliver the electrical stimulation signals to the electrode.

Various embodiments of the present disclosure are directed toward a method of auricular stimulation. A stimulation location is determined from anatomic points of an ear of a subject. An earpiece, having a stimulation electrode, is positioned so as to locate the stimulation electrode in a location corresponding to the stimulation location. A series of electrical stimulation signals are delivered to the stimulation electrode according to a stimulation profile. The stimulation profile is adjusted in response to feedback indicative of the effectiveness of stimulation of the auricular branch of the vagus nerve for mitigation of inflammatory disease processes. The stimulation profile can also be adjusted for mitigation of the disarray in which the neural control of the heart is placed when it is in presence of an ischemic or microischemic event.

Embodiments of the present disclosure include one or two auricular stimulation device kits. The kit includes a first earpiece having an electrode configured and arranged to deliver a series of electrical stimulation signals to a first auricular location that corresponds to a first one of a plurality of categories of persons, the categories of persons being based upon physiological features. A second earpiece has an electrode configured and arranged to deliver the series of electrical stimulation signals to a second, different auricular location that corresponds to a second, different one of the plurality of categories of persons. A pulse-generator circuit is configured and arranged to generate the series of electrical stimulation signals, and deliver the electrical stimulation signals to one of the first and second earpieces.

In accordance with certain embodiments, one auricular nerve (or nerve region) is stimulated in a patient at a time, and in other embodiments both auricular nerves (or nerve regions) are stimulated in the auricular areas of the right and left ears. Depending on the desired/measured effect, the stimulation in each ear can be sequential, simultaneous and/or have other relationships relative to phase, frequency, and amplitude or duty cycle. Although various embodiments herein are described in the context of a single one auricular nerve in one ear being stimulated, the various teachings can be applied to the stimulation of both auricular nerves.

The above summary is not intended to describe each illustrated embodiment or every implementation of the present disclosure. The figures and detailed description that follow more particularly exemplify various embodiments.

BRIEF DESCRIPTION OF THE DRAWINGS

Various example embodiments may be more completely understood in consideration of the following detailed description in connection with the accompanying drawings, in which.

Figure 1:
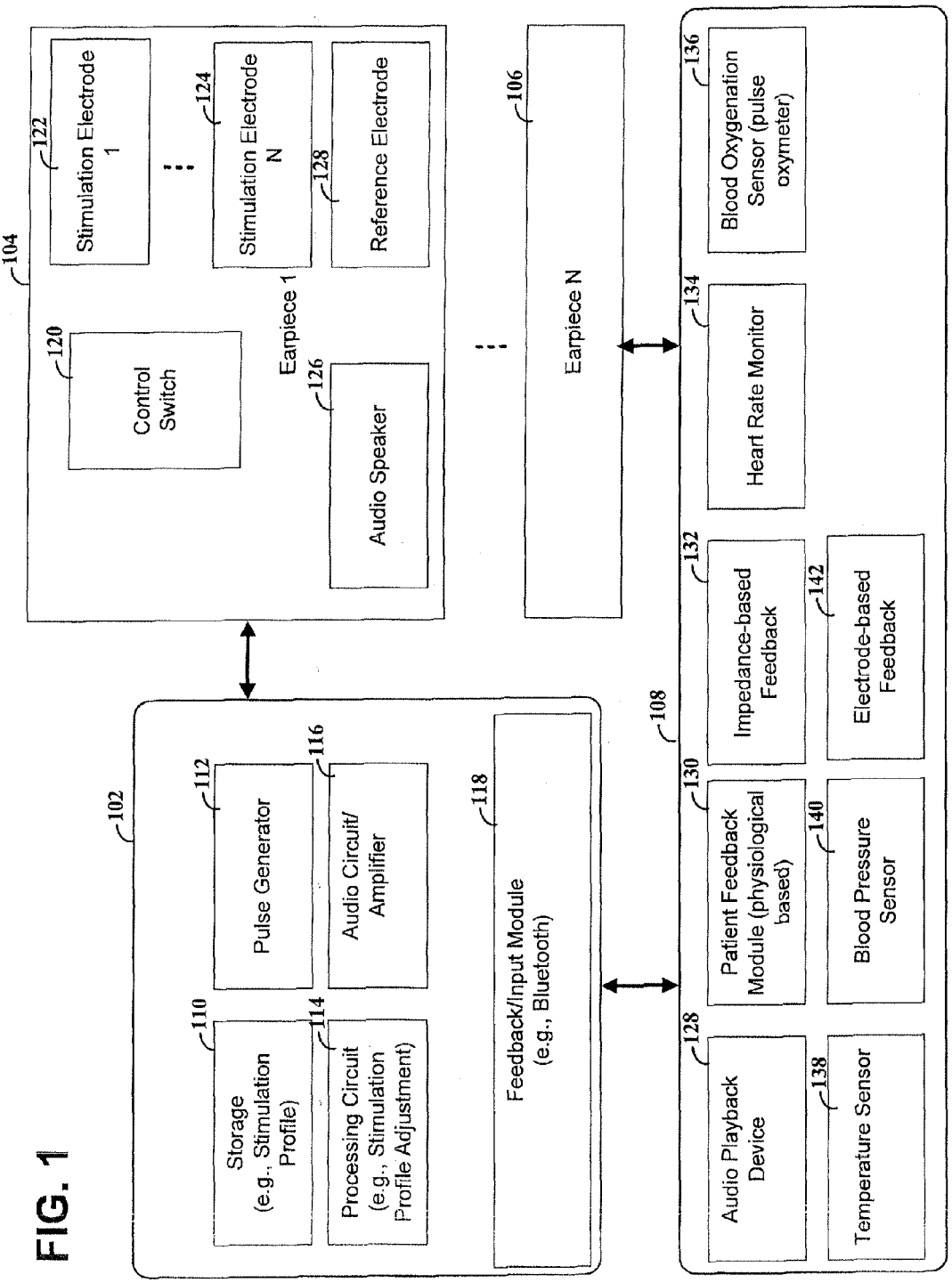
FIG. 1 depicts a block diagram for a system for providing stimulation of the auricular branch of the vagus nerve, consistent with embodiments of the present disclosure.

While the disclosure is amendable to various modifications and alternative forms, examples thereof have been shown by way of example in the drawings and will be described in detail. It should be understood, however, that the intention is not to limit the disclosure to the particular embodiments shown and/or described. On the contrary, the intention is to cover all modifications, equivalents, and alternatives falling within the spirit and scope of the instant disclosure.

DETAILED DESCRIPTION

The present disclosure is believed to be applicable to a variety of different types of devices and processes, and the present disclosure has been found to be particularly suited for stimulation of one or both of the auricular branches of the vagus nerve. While the present disclosure is not necessarily limited to such applications, various aspects of the present disclosure may be appreciated through a discussion of various examples using this context.

Various embodiments of the present disclosure are directed toward locating a stimulation point for providing electrical stimulus to one or both of the auricular branches of the vagus nerve. Particular aspects relate to facilitating methods for providing therapeutic levels of such stimulation in a reproducible manner. For instance, certain embodiments are directed toward a stimulation-providing device that has a positioning and fixation device that is designed to consistently deliver individualized (operator-independent) electrical stimulation to the auricular nerve with the objective of activating the parasympathetic system and decreasing the sympathetic/parasympathetic balance to decrease and/or slow down the inflammatory process and/or stop degenerative processes triggered by the neural network that controls the heart during periods of stress, such as those that occur during the progression of heart failure, dilation of the ventricles and its reaction to a sudden decrease in regional blood flow in the myocardium.

Particular embodiments of the present disclosure are directed toward non-invasive techniques for vagal stimulation based on auricular nerve stimulation that address or mitigate problems such as a requirement for active operator involvement, the need for highly skilled and poor reproducibility of stimulation results (e.g., from patient to patient or from stimulation session to stimulation session). Without being limited by theory, it is believed that widespread clinical use has been frustrated by a failure to recognize issues with proper stimulation delivery outside of the specialized centers and without highly trained operators.

Embodiments of the present disclosure are directed toward an auricular stimulation device kit. Different configurations of the kit allow for either single side auricular stimulation, dual side auricular stimulation, or both. Although various embodiments are discussed in the context of single side kits, it is recognized that dual side kits can be used in place of a single side kit for many applications and embodiments. The kit can include a first earpiece (and a second earpiece) that has an electrode configured and arranged to deliver a series of electrical stimulation signals to a first specific auricular location. The first specific location corresponds to a first one of a plurality of categories of persons. The categories of persons are based upon physiological features. For instance, the categories can be based upon measurements of a patient's body (e.g., ear lobe morphology, facial features, height and/or weight). The kit also includes at least a second earpiece that has an electrode configured and arranged to deliver the series of electrical stimulation signals to a specific second, different auricular location that corresponds to a second, different one of the plurality of categories of persons. A pulse-generator circuit is configured and arranged to generate the series of electrical stimulation signals, and deliver the electrical stimulation signals to either one of the first and second earpieces.

The kit can be used to select an earpiece that is designed to match the patient's physiological features and therefore be more likely to provide the electrical stimulation signals. For instance, it has been discovered that physiological features can provide helpful indicators of optimal locations for stimulation of the auricular branch of the vagus nerve. In this manner, a number of different earpieces can be designed with different electrode placements that correspond to the optimal locations, which are selected based upon the physiological features of a particular patient.

Other embodiments of the present disclosure are directed toward an auricular stimulation device that has an earpiece with an electrode arrangement. The electrode arrangement is configured and arranged to deliver a series of electrical stimulation signals to an auricular location. A pulse-generator circuit is configured and arranged to generate the series of electrical stimulation signals having a stimulation profile, and to deliver the electrical stimulation signals to the electrode arrangement. A sensor is configured and arranged to generate a feedback signal that is responsive to the electrical stimulation signals. A feedback circuit is configured and arranged to modify the stimulation profile in response to the feedback signal. In this manner, the auricular stimulation device can dynamically modify the stimulation provided to a patient.

For instance, a first stimulation profile may include a series of square wave pulses having a voltage or current level 'X'. The feedback signal may detect a certain impedance level at, or near, stimulation point(s) of the electrode arrangement. The stimulation profile can then be adjusted by increasing or decreasing the voltage or current level 'X'. This process can repeat in response to further feedback and thereby achieve and maintain the stimulation profile within an acceptable level.

The use of impedance as a feedback can be particularly useful for indicating whether or not a stimulation electrode has an adequate electrical connection with the patient. For instance, the impedance measurement can be taken between the simulation electrode and a reference electrode, which can be placed in contact with the patient at another location. The impedance measurement between the stimulation and the reference electrodes can be used to generate a report as to whether the electrode and its support material have been correctly placed and/or to indicate other potential problems (e.g., poor electrical conductivity caused by improperly cleaned contact areas).

In other instances, the first stimulation profile can be modified relative to one or more different parameters. This can include changes to one or more of the pulse duration, pulse frequency, duty cycle and total stimulation duration. This can also include changes to the pulse shape (e.g., changes to edge rates or pulse shapes having saw tooth, triangle or sinusoidal properties).

Consistent with particular embodiments, the pulse-generator circuit can be configured with predetermined stimulation profiles. The feedback circuit can then be used to select from the various predetermined stimulation profiles. In one mode, the pulse-generator circuit can be set to cycle through different ones of the predetermined stimulation profiles. The results of the stimulation profiles can be monitored and used to select a particular stimulation profile for future use. In another mode, the pulse-generator circuit can be configured to select a particular stimulation profile based upon the feedback without first cycling through different stimulation profiles.

Another aspect of the stimulation profile can include spatial location of the delivery stimulus. For instance, the electrode arrangement can have multiple electrodes that are separately addressable for delivering the electrical stimulation. The particular electrode used for stimulation can be selected based upon feedback. For instance, multiple electrodes can be used to sequentially provide stimulation and the electrode that produces the best feedback can be selected for subsequent stimulation. In some instances, the selection can include the selection of more than one electrode. For instance, the optimal location may reside between two different electrodes and therefore the stimulation may be more effective if both of the electrodes are used relative to either electrode individually.

Certain embodiments of the present disclosure are directed toward feedback provided by a patient. For instance, a patient can provide an indication when noticeable effects occur from the stimulation. This can include, but is not limited to, a tingling sensation and/or pain resulting from the stimulus.

Although not limited by theory, aspects of the present disclosure are directed toward stimulating the auricular branch of the vagus nerve for studying and/or treating inflammatory diseases, such as arthritis, colitis, ischemia, myocardial infarction, depression, obesity, Alzheimer and congestive heart failure. Specific experimental embodiments of the present disclosure relate to the surprising discovery that stimulating the auricular branch of the vagus nerve using the particular methods and techniques provided in the present disclosure can be particularly useful for studying and/or for chronic treatment of hypertension in a reproducible manner.

In another embodiment, the specialized location is used for placement of an electrode of a multiple electrode array. The specialized location is selected based upon a feedback indicating that the location produces a desired therapeutic response. This feedback can be used to select a disposable or reusable earpiece with a single electrode, from a catalog of available standard one-electrode earpieces. The use of single electrode earpieces can be particularly useful for providing reduced cost devices (e.g., relative to a more complex a multiple electrode earpiece). In this manner, a particular type of standard earpiece can be prescribed for the patient and used for chronic treatment.

Consistent with experimental embodiments, stimulation of the auricular branch of the vagus nerve can be accomplished using an auricular device that includes a physical support structure for a stimulation electrode. The auricular device can be constructed from a flexible adaptive material. In certain embodiments, the auricular device can be tailored to each individual patient's anatomy to facilitate correct and reproducible placement of the stimulation electrode. This facilitates consistent stimulation of the auricular branch of the vagus nerve relative to a patient's particular anatomy and to an operator's anatomical skills. The auricular device can also include an impedance meter configured and arranged to measure the impedance between the stimulation electrode and a reference electrode. This measurement can then be used to inform the operator that proper placement and contact of the electrode has been achieved in the desired region of stimulation.

Aspects of the instant disclosure utilize a portable controlled current stimulator with specific stimulation wave characteristics to control arterial pressure. Methods and devices, consistent with the instant disclosure, utilize the portable controlled current stimulator for supporting the stimulation electrode to enable reproducible and operator independent stimulation of the auricular branch of the vagus nerve.

Turning now to the figures, FIG. 1 depicts a block diagram for a system for providing stimulation of the auricular branch of the vagus nerve, consistent with embodiments of the present disclosure. The various components depicted in FIG. 1 are provided by way of example and are not necessarily limiting. For instance, one or more of the depicted components are optional and can be removed, replaced or modified for a particular application. In other instances, additional components, circuits and/or functionality can be added to the system.

Device 102 includes circuitry 112 that is configured and arranged to generate electrical stimulation signals (e.g., pulses) that are consistent with a desired stimulation profile. A processing circuit 114 can adjust the stimulation profile in response to one or more inputs. Consistent with certain embodiments, the adjustment to the stimulation profile can made by selecting from a set of stimulation profiles, which can be stored in a storage/memory circuit 110. Consistent with other embodiments, the adjustment can be made using an algorithm that determines parameter changes to the stimulation profile.

Audio circuit/amplifier 116 can be included to generate audio signals for delivery to an earpiece 104, 106 and for generation of sound by speaker(s) 126. The audio signals can be designed for therapeutic purposes or functional purposes (e.g., music or cellular phone). For instance, feedback/input module 118 can receive audio signals from an external source. Audio circuit 116 can then amplify, or otherwise condition, the received signals before they are transmitted to the earpiece 104.

Structure/earpieces 104, 106 contain one or more stimulation electrodes 122, 124 configured and arranged to deliver electrical stimulation signals to the auricular branch of the vagus nerve. A control switch 120 can be used to select between the stimulation electrodes. In this manner, the electrical stimulation can be delivered to different stimulation locations relative to the patient. A reference electrode 128 can also be included. This reference electrode can be used to provide feedback information, such as an electrical impedance measurement taken relative to the stimulation electrodes.

Embodiments of the present disclosure are directed toward the use of an earpiece 104 that is specially made for an individual patient. For instance, various embodiments include an earpiece that was constructed by constructing a mold of the patient's ear and then casting the earpiece from the mold. Examples of such embodiments are discussed in more detail herein.

Other embodiments of the present disclosure are directed toward a kit that includes multiple types of earpieces 104-106. Each earpiece type can be constructed with parameters corresponding to different individuals. For instance, the physical shape and size of the earpiece can vary between each type of earpiece. Another variable can be the location of the stimulation electrode(s) and, if present, a reference electrode. Each type of earpiece can then be correlated to a category of persons having similar physiological features. These physiological features can be measured for an individual and be used to select an earpiece that most closely matches the measured features. Alternatively or in addition, a patient could try out multiple different earpieces and feedback from tests could be used to help select an appropriate earpiece for subsequent use. Consistent with certain embodiments, the different types of earpieces are configured for different auricular locations for different categories of persons. Other variations in earpieces can relate to the monitoring/sensing capabilities of the earpieces. For instance, an earpiece that is used to treat hypertension can be configured and arranged to include a sensor for monitoring the heart rate of an individual.

Consistent with embodiments of the present disclosure, the system can include circuits, sensors and devices 108 to provide input and/or feedback to the device 102. For instance, an audio (playback) device 128 can provide audio signals to the device 102. This can be useful to provide music, therapeutic tones and/or for cellular telephone conversations. This could also help with patient compliance with the treatment by incorporating the stimulator into his/her daily activities of cellular phone use, music listening or TV watching. Other audio sources are also possible. In other instances, feedback can be provided to facilitate the treatment of a patient. This can include, as non-limiting examples, temperature sensing 138, blood pressure monitoring 140, patient feedback 130, electrical impedance measurement 132, feedback from a stimulating electrode 142, heart rate monitoring 134 and/or blood oxygenation sensing 136. Accordingly, monitored parameters can include one or more of heart pulse waves, heart sounds, heart ballistocardiogram, and heart rate variability with respect to time and frequency analysis of the beat to beat intervals, arterial pressure parameters, core temperature and local temperature. These and other inputs can be used for a variety of purposes including, but not limited to, selection of a stimulation profile.

Embodiments of the present disclosure are directed toward the methods, devices and systems for quantifying the efficacy of the transcutaneous stimulation of the neural system relative to associated effects on the inflammatory system. For instance, particular embodiments are directed toward the stimulation of the auricular nerve in its terminal located in the pavilion of the ear. Quantifying such aspects of transcutaneous stimulation can be accomplished using a variety of different approaches. Consistent with one such approach, Response Surface Methodology (RSM) is employed. RSM includes several different mathematical and statistical techniques for modeling and analysis of a response of interest that is influenced by multiple variables. The objective of RSM is to optimize the response relative to the variables. For examples of RSM techniques and applications, reference can be made to Montgomery, Douglas C. 2005. *Design and Analysis of Experiments: Response surface method and designs*. New Jersey: John Wiley and Sons, Inc., which is fully incorporated herein by reference. A response surface is an output generated as a function of input parameters. A response surface may use the mathematical relationship to express the output in the form of data, graph, table, computed numerical output value, or other useful output. A response surface is not limited to two-dimensional or three-dimensional surfaces. The response surface can have additional dimensions corresponding to additional parameters and/or factors.

Consistent with an embodiment of the present disclosure, a response surface can be created that represents the systolic arterial pressure (e.g., reflecting the degree of parasympathetic activation achieved by the stimulation of the auricular nerve) as a function of input variables. In other embodiments, a response surface can be created that represents the heart rate or the diastolic pressure.

Consistent with other embodiments of the present disclosure, a response surface can represent pain thresholds corresponding to variables such as levels of current intensity and electrode location, related to locations of nociceptive receptors, for example. A response surface may be a two-dimensional output of surrogate variables that reflect the effects of neural stimulation on the inflammatory system determined from any number of input magnitudes. A stress threshold may then be established. Above the threshold current, the pain experienced by the patient may be undesirable, indicating that a change to the prescription for that particular patient may be prudent.

Other examples of response surfaces in accordance with the present disclosure include data that describes one or more of the following: the magnitude of the ratio of the energy components of the Fourier spectrum of the high-frequency over the low-frequency energy components of the heart rate variability as a surrogate variable of the parasympathetic/sympathetic balance of the autonomic system; the change in systolic and diastolic arterial pressure; the change in heart rate; or other desired output as a function of predetermined input parameters. In the chronic setting, a possible output variable could be the level of the C-reactive protein present in blood or other appropriate surrogate variables that can be used to track changes in the inflammatory system. For example, an input parameter can include vectors (amplitude and angle) that define the distance between a reference site and the actual stimulation site for a particular combination of ear lobe anatomy.

Another potential input parameter can include where one of several electrode earpieces/support structures is used, relative to a selection of different earpieces having different electrode placements and/or shapes. A particular set of anatomy parameters of patients can also be used (e.g., a surface level three-dimensional reconstruction of the ear lobe region of interest including anatomical location of the auricular nerve).

In one instance, the input variables could include aspects of the electrical stimulus including, but not necessarily limited to, pulse width, pulse shape, voltage level, current level and/or duty cycle. In another instance, the input variables could include electrode placement relative to anatomical features of a patient. With respect to the electrode placement, aspects of the present disclosure provide an objective measurement that relates to the distance of the actual stimulation site to a reference site determined from anatomical features of a patient's ear.

Response surface data may be generated using a mathematical relationship between the initial inflammatory state and the desired state. For example, the mathematical relationship may be a polynomial equation having any number of terms and cross-terms. In a further example, the mathematical relationship may include a calculation of changes in the state of the inflammatory system using empirical measurements from pressure sensors, or indirect pressure sensors (e.g., pressure wave velocity propagation), from electrocardiographic measurements (e.g., the heart rate HR (in beats per minute) which is calculated by dividing 60 by the time (T, in minutes) between detected R waves of the ECG) or from blood concentration of appropriate markers of the status and/or change of the inflammatory system.

Figure 2:
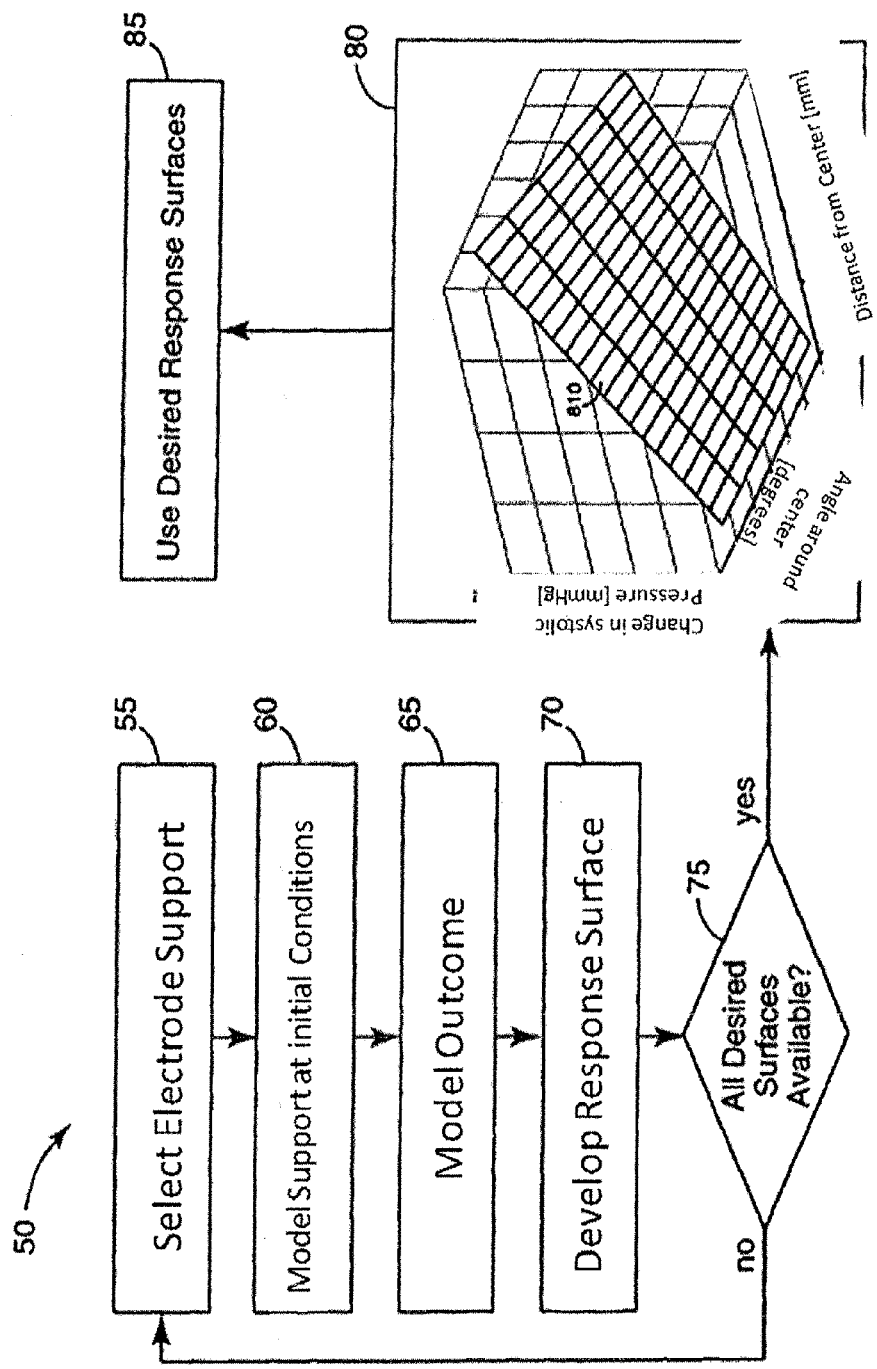
FIG. 2 depicts a flow diagram for developing response surfaces and using the response surface in accordance with embodiments of the present disclosure.

FIG. 2 depicts a flow diagram for developing response surfaces and using the response surface in accordance with embodiments of the present disclosure. The process flow 50 can be used to generate response surfaces, such as a response surface 80. Such response surfaces can be particularly useful for analysis of treatments (e.g., the inflammatory response) using mathematical algorithms. This analysis can be used for the treatment planning and electrode support system analysis and validation for transcutaneous neural stimulation. In some instances, results can be automatically generated without a physician or medical personnel having to perform an analysis for each patient. For instance, medical personnel can utilize advantages of the computational power of a computer and associated numerical methods, without having to learn methods such as finite elements analysis or Fourier transformations and without the need for a computational platform such as a computer aided design (CAD) and/or computer aided engineering (CAE) system.

It has been recognized that the effect of the neural stimulation over the inflammatory system can be significantly influenced by the distance between the stimulation site and the nearest nociceptive neural receptor that will determine the pain threshold and thus the ability of the physician or medical personnel to increase the stimulation current to the necessary level for achieving the desired response. It has also been recognized that poor coupling of the stimulation electrode to the skin can have significant impact (e.g., making impedance measurements a valuable tool for confirming proper treatment and for identifying problems with grease, wax or other interfering substances).

Consistent with certain embodiments of the present disclosure, a manufacturer of standard earpiece appliances can provide data representing the response surfaces expected for each appliance in a form that allows the device or its programmer system to combine them with anatomical parameters that the medical personnel can determine for each patient (e.g., by measuring the morphology of an ear lobe). A particular earpiece can then be selected. Other input parameters, such as a determination of the pain threshold, can also be used to provide the medical personnel with an expected overall response surface that will allow them to predict which appliance will deliver the desired effect. For some two sigma anatomies, such an analysis may indicate that none of the standard appliances will deliver the desired effect and that an individual cast will need to be made from the patient's ear to be able to manufacture an individualized electrode support system for that patient. For instance, the coordinate axis may be representative of the x-y planar distance between the reference point and the response may be either change in arterial systolic pressure, heart rate or heart rate variability ratio (ratio of the energy of the high-frequency component of the Fourier analysis of the R-R interval and its low-frequency component.

According to certain embodiments of the present disclosure, medical personnel can be provided with the appliance dependent aspects of the response surfaces by a manufacturer of the electrode support appliances, or by an organization that performs the necessary numerical analysis, as examples. As a non-limiting example, a manufacturer can provide the response surfaces to the medical personnel. Following the flow chart of FIG. 2, the manufacturer can select (55) an electrode support system (appliance) for modeling. The manufacturer of appliances can then choose to provide a set of response surfaces for a number (e.g., one hundred) of the most common anatomical configurations of the cavity of conchae and its limiting regions such as the crus of helix, the tragus and the antitragus for each appliance manufactured (different shapes and sizes targeted to optimally cover most anatomies of the cavity of conchae, crus of helix, tragus and antitragus).

The appliances can then be modeled at the initial conditions (60), and the model is analyzed using the average response observed empirically (65) in the past for each anatomical pattern and a set of model outcomes is obtained, one outcome for each anatomical pattern. Modeling of anatomical patterns of the cavity of conchae, crus of helix, tragus and antitragus can include implicit elastic properties of the electrode support system or appliance, cavity of conchae, crus of helix, tragus and antitragus. Parameters may then be varied, like the elasticity of the tragus and one or more response surfaces created that represent the response to the variation(s).

The medical personnel, as a non-limiting example, takes three pictures of the ear lobe: a front picture, a picture from a 45 degrees posterior view and a picture from 45 degrees anterior view. These pictures are fed in any standard format (JPEG, GIF, etc.) to the stimulation apparatus and or its programmer alongside the response surfaces provided by the manufacturer for its appliances. The apparatus or its programmer will extract the anatomic parameters of the ear lobe in a similar manner as parameters are extracted for facial recognition software, knowledge that is common in the face recognition art. Other approaches are available to transform the anatomy of the ear lobe and the cavity of conchae and its limiting regions into a set of parameters, including a three-dimensional picture and direct measurements of distances between anatomically characteristic structures.

The desired change in the status of the inflammatory system in terms of the selected surrogate variable (as a non-limiting example arterial systolic pressure) can then be selected or determined. From this information, a list of one or more appliances can be used for those appliances that are suitable for the identified purpose. If no suitable appliances are available, an individually-casted electrode support appliance can be recommended for that particular patient.

As a non-limiting example, a change in arterial systolic pressure can be the desired result/purpose of a treatment involving an alteration of the inflammatory system to the desired state. A response surface may be provided that provides the expected change in systolic arterial pressure as a function of the stimulation current for the patient's particular anatomy of the cavity of conchae, crus of helix, tragus and antitragus. The patient's age can be a relevant factor in the response surface, and the patient's health or lack thereof and the specific pathologies affecting him/her can also be important factors. Accordingly, a response surface can be generated that determines the rate of change in the selected surrogate variable (i.e., the variable selected to indirectly monitor the effect that the stimulation is having over the status of the inflammatory system) as a function of the electrode position for different age groups or disease factors (e.g., Congestive Heart Failure Class I, II, III, IV; systolic versus diastolic dysfunction; hypertension versus normotensive or Hypertrophic Obstructive Cardiomyopathy versus none). As additional factors are identified, response surfaces may be determined for each factor, group of factors and cross-factors.

Optionally, the device or its programmer could be connected continuously or sporadically to the Internet and the manufacturers could update the existing response surfaces as new data is added to their databases and add new ones. Moreover, the devices or their programmers could be also transmitting the new empirical data that is obtained during the treatment planning, treatment verification or actual treatment delivered to the patients back to the manufacturers so that their databases of actual versus predicted response surfaces improve continuously.

If all the desired surfaces have not been created at a decision 75, then other parameters are used and/or other appliances are selected, and steps 55, 60, 65 and 70 are repeated for the new parameters. After all desired response surfaces have been created, the response surfaces 80 are provided to the physician's device or programmer for that device, such as a device programmer, to use (85) the desired response surfaces for decision-making with the assistance of the device or its programmer.

Certain embodiments recognize that a response surface can indicate desired stimulation profiles that do not produce measurable, significant and/or immediate macro level changes. For instance, a response surface may be generated in which a short term change in arterial systolic pressure is detected at a certain threshold level of stimulation (e.g., levels for voltage, current, frequency and/or time). The response surface can indicate that therapy can be efficacious at lower levels of stimulation even though there may not be measurable macro level effects. Notwithstanding, monitoring of various macro level changes can be used for a variety of additional purposes including, but not necessarily limited to, identification of the correct electrode (location) to use to stimulate the auricular nerve (or the location of the auricular nerve), verification of good electrical contact between the device and the electrode and/or determining a stimulation level. For example, response surfaces 80 can be generated by monitoring measurable macro level changes. A particular electrode and stimulation waveform can be selected from this information. The level of stimulation can, however, be set as a function of a threshold level determined for causing measurable macro level changes (e.g., as a percentage or set amount less than the threshold level).

Without being limiting, a clinical implementation for the treatment of emergency patients who report the symptoms of a possible myocardial infarct (i.e., chest pain) can be treated in the following way using the teachings in the present application. First, an emergency response team is dispatched to the patient's location. The team then stabilizes the patient and initiates bilateral auricular nerve stimulation using a complex multiple electrode support appliance discussed herein, while connecting the patient to the complex unit capable of physiologic parameter analysis (heart rate, blood pressure, heart rate variability, body temperature, pulse oxymmetry, etc.). During the trip to the emergency service center for further diagnosis and treatment, the complex support appliance (automatically) determines desired stimulation parameters and electrode configuration. This information can then be used to identify and recommend the standard appliance to be used for further treatment of the patient. Upon arrival to the emergency service center, the data is automatically or manually communicated to a treatment center, where the patient can now be switched to the correct standard stimulation support system chosen from the catalog at the appropriate time, considering the other therapeutic and diagnostic maneuvers required for his/her treatment. The standard units, with the standard electrode support appliances, could alternatively be packaged with the angioplasty catheters for their deployment if the infarct diagnosis is confirmed or with stents for ease of use of the treating medical personnel. The battery of the standard unit can be packaged with the angioplasty catheter or with the stent could be designed to last for (days or weeks of) continuous or sporadic treatment. Other units could be made available to the patient for longer term treatment when indicated by the physician due to high risk of a second infarct.

Figure 3:
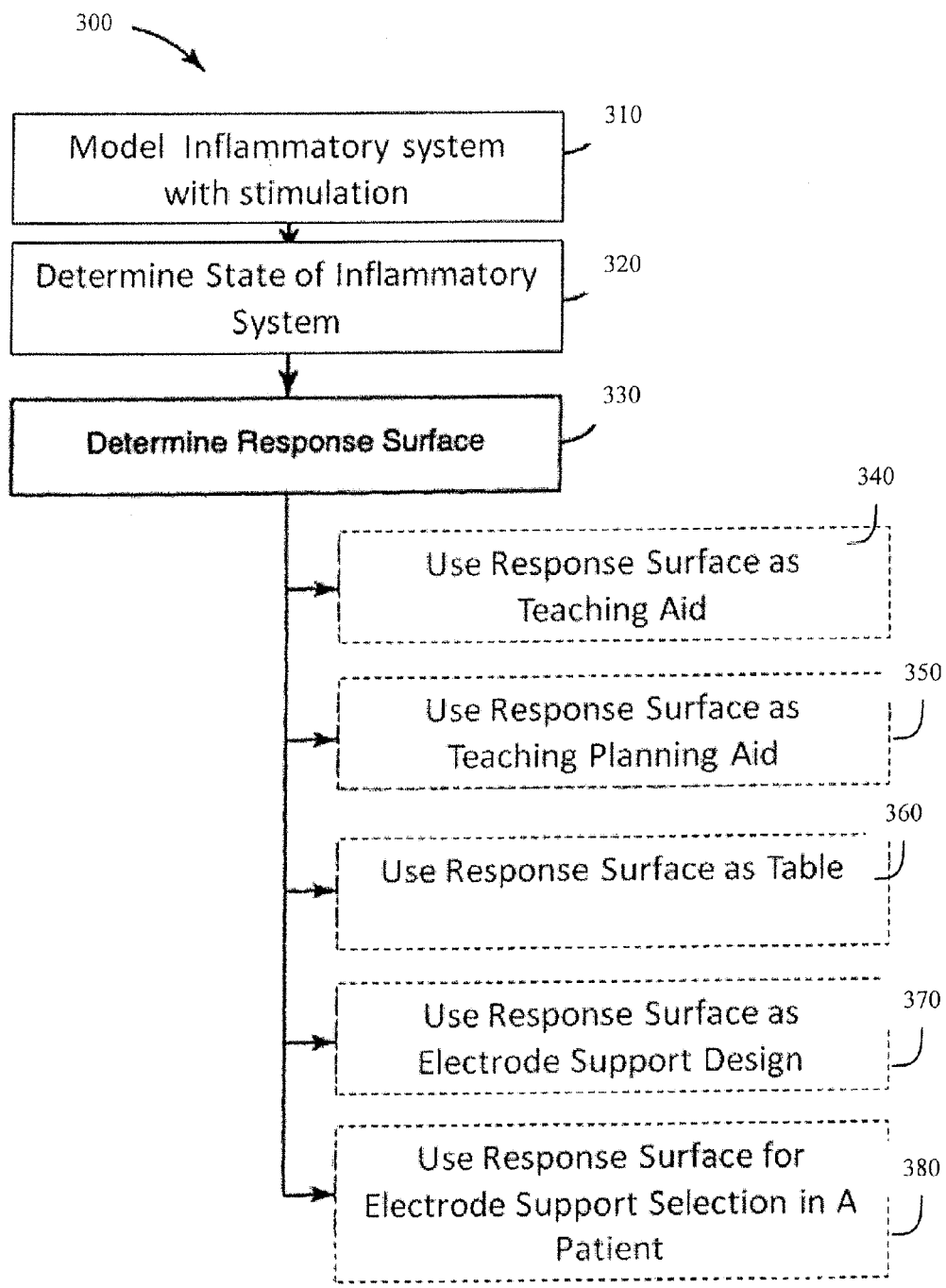
FIG. 3 illustrates a flow diagram for determining a response surface, consistent with embodiments of the present disclosure.

FIG. 3 illustrates a flow diagram for determining a response surface, consistent with embodiments of the present disclosure. The flow diagram 300 is discussed herein in the context of a change in arterial systolic pressure during a stimulation procedure; however, the flow diagram 300 can also be used in connection with other desired results stemming from an alteration of the inflammatory system. Each electrode support appliance and/or family of appliance type and/or grouping of appliances may be associated with one or more response surfaces. The modeling (310) can be made with respect to a particular appliance or family of appliances, such as by creating a three-dimensional solid model in CAD/CAE workstations. The model may then be analyzed 320, such as by using numerical methods, to determine one or more response surfaces 330 for an average anatomy or for a set of anatomies of the region of interest in the external ear.

Consistent with embodiments of the present disclosure, a family of response surfaces may be generated such that the output of the response surface, e.g., arterial systolic pressure, can be determined for a prescribed electrode support appliance undergoing prescribed stimulation intensity in a pre-chosen anatomy of the predetermined set. In this way, the response surfaces can be generated independent of the specific patient and/or specific prescription, thereby reducing the need for complex modeling and computational capabilities at the physician's office, for example. Alternatively, mathematical algorithms intermediate to the final response surface could be generated by the manufacturer, ready to be used and combined at the physician's office with the individual anatomical data provided by the physician about his patient.

The response surfaces 330 may be useful for a variety of applications in accordance with the present disclosure. The response surface data may be generated as a teaching aid 340, a treatment planning aid 350, a table 360 (e.g., a look-up table, either provided as numerical data stored in a memory, or as a print-out, 2D and/or 3D and/or multidimensional surface in a display or graphic tablet), or other useful forms. The table 360 may be incorporated into a database where the expected response surface can be compared with the actual response surface and used to either improve the model used to derive the response surface and/or to improve the completeness of the empirical database of response surfaces. This can be particularly useful for the identification and accounting of new factors and cross-factors assuring the continuous improvement of the clinical prescriptions given to patients.

Embodiments can further involve designing (370) an electrode support appliance using the generated response surface data. In other embodiments, methods may involve using the generated response surface data to select (380) an appliance suitable for effecting changes in the systolic arterial pressure from the initial value to the desired value.

It may be useful in other embodiments in accordance with the present disclosure to provide patient-specific information as an input to a system that generates response surfaces. Examples of patient specific input include, but are not limited to: patient age, patient disease state for cardiovascular and neural systems, patient's infectious state, presence of cancer, pregnancy status, patient pain tolerance level, other compromised health attributes, patient's ear lobe anatomy parameters (e.g., obtained as pictures of the ear lobe sufficient to extract through software analysis a 3D reconstruction of the cavity of conchae, or other reconstruction methods), or other patient related information where patient-specific response surfaces are desired.

In various embodiments, interim patient changes in the surrogate variable can be used to gage the changes effected in the inflammatory system as input parameters for response surface generation. For example, a patient at an interim treatment stage and a particular prescription may not be producing expected results. The patient's interim systolic arterial pressure changes can be modeled and provided as feedback into the response surface generation system, along with current prescription information. An analysis can be run on the response surface generation system along with current prescription information. An analysis can be run on the response surface generation system, and nerve position or other parameters can be adjusted or added, such that a new set of response surfaces are provided that are consistent with the patient results at the interim positions. The revised response surfaces can then be used to generate a new prescription for the individual patient that more accurately reflects results of the particular appliance used in that patient. Moreover, this analysis might indicate that the patient needs to be treated using a different electrode support appliance. Embodiments of the present disclosure are directed toward the movement of this information to the appliance's manufacturer and back to the physician's office and device or device's programmer through the Internet or other means in order to ensure that the physician and the manufacturer are continuously improving the quality of the prescription and of the therapy being delivered to the patient.

Figure 4:
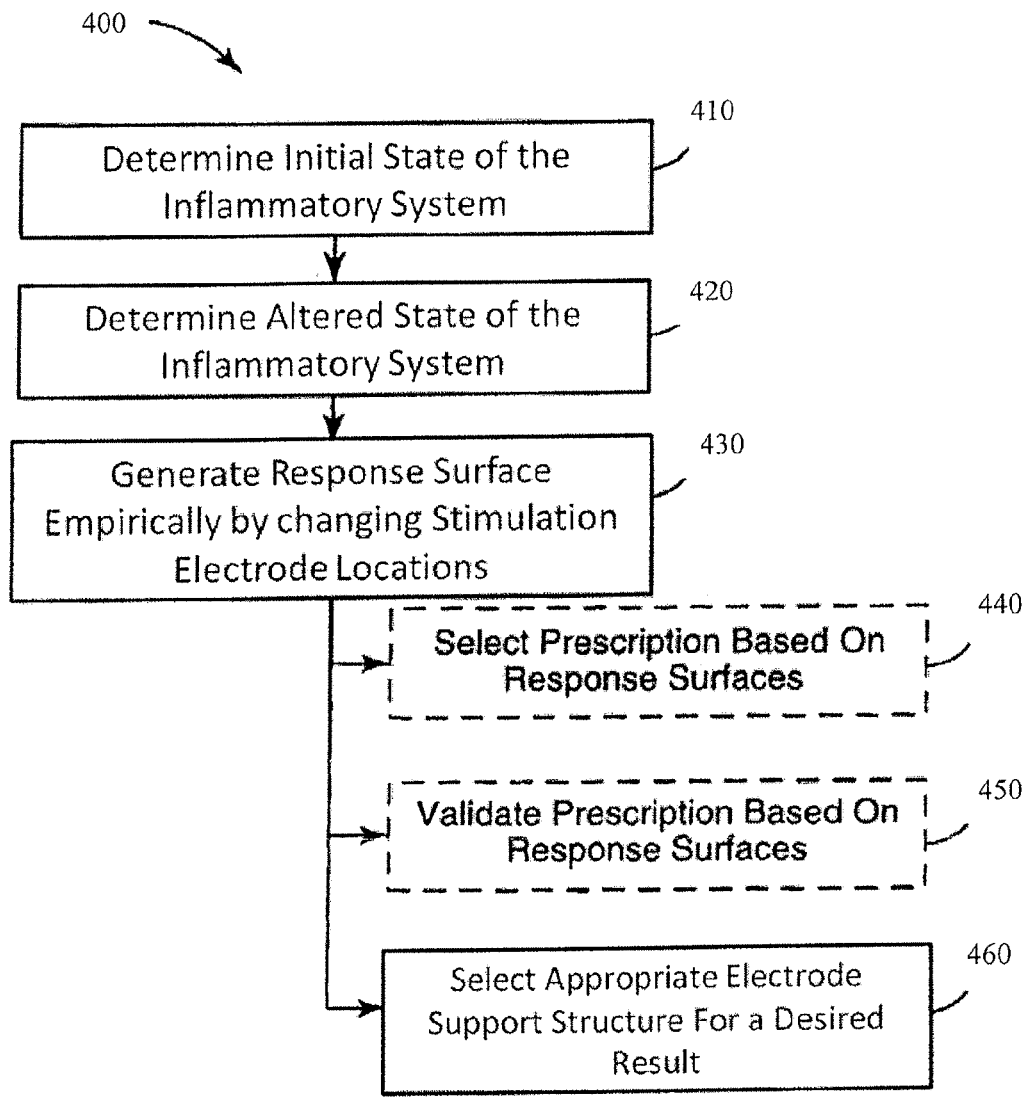
FIG. 4 depicts a flow diagram for determining change of the state of the inflammatory system in accordance with embodiments of the present disclosure.

FIG. 4 depicts a flow diagram for determining change of the state of the inflammatory system in accordance with embodiments of the present disclosure. Particular, non-limiting uses for the flow diagram for FIG. 4 include determining systolic arterial pressure changes and selecting electrode support appliance using response surfaces. For instance, FIG. 4 depicts an empirical method/algorithm 400 useful for determining changes in the state of the inflammatory system. This algorithm can include the determination (410) of an initial state of the inflammatory system. This initial state can be, for example, the systolic arterial pressure, the diastolic arterial pressure, the heart rate, the heart rate variability ratio, and or combinations thereof. A desired state of the inflammatory system is also determined 420. Response surface data can then be generated 430. In some embodiments, this response surface data can be determined from actual measurements of the changes of these variables for one or more an individual patients. For instance, the patient can be stimulated with the highest current possible below the pain threshold and using a multi-electrode electrode support appliance.

Embodiments of the present disclosure are also directed toward the selection of a prescription (440) based on the generated response surface data (430). In other embodiments, the generated response surface data can be used to validate (450) a proposed prescription, or to select an appropriate electrode support structure for a desired result (460). For example, a response surface can indicate that the desired change that occurred with a particular electrode or electrode combinations where the pain threshold was high enough (i.e., larger distance to nociceptive receptor, but closer distance to auricular nerve), thus enabling the physician to select a standard support structure that has that particular electrode or electrode combination.

Figure 5:
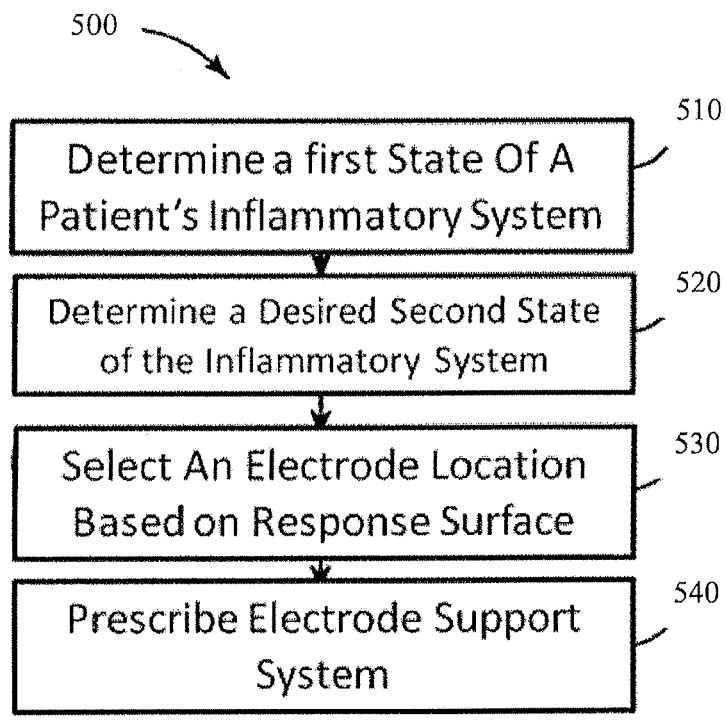
FIG. 5 depicts a flow diagram of an algorithm relating to treatment planning for diseases affected by the inflammatory system in accordance with embodiments of the present disclosure.

FIG. 5 depicts a flow diagram of an algorithm relating to treatment planning for diseases affected by the inflammatory system in accordance with embodiments of the present disclosure. A transcutaneous neural treatment planning method 500 involves determining (510) a first state of the inflammatory system, determining (520) a desired second state of the patient's inflammatory system, selecting (530) one or more response surfaces based on the determined first and second states of the patient's inflammatory system and prescribing (540) one or more electrode support appliances based on the one or more response surfaces, the one or more response surfaces indicating that the prescription is acceptable.

Determining (510) the first state of a patient's inflammatory system may be done, for example, by assessing the patient's heart rate, heart rate variability, high to low frequency ratio of the energy components of the heart rate variability, arterial systolic pressure and/or arterial diastolic pressure. These variables, alone or in conjunction, can thereby define the initial state of the inflammatory system.

Once the initial state is determined, the physician can indicate the minimum/maximum/desired changes that he/she wants to see from the initial state. These changes, where the inflammatory system activity is changed/reduced, can be represented by a decreased heart rate, and/or a reduced systolic arterial pressure, and/or a reduced diastolic arterial pressure, and/or a decreased temperature, and/or an improved heart rate variability profile indicating a larger activity of the parasympathetic system. If the final state requires large changes, those changes may be divided into several smaller incremental adjustments.

Figure 6:
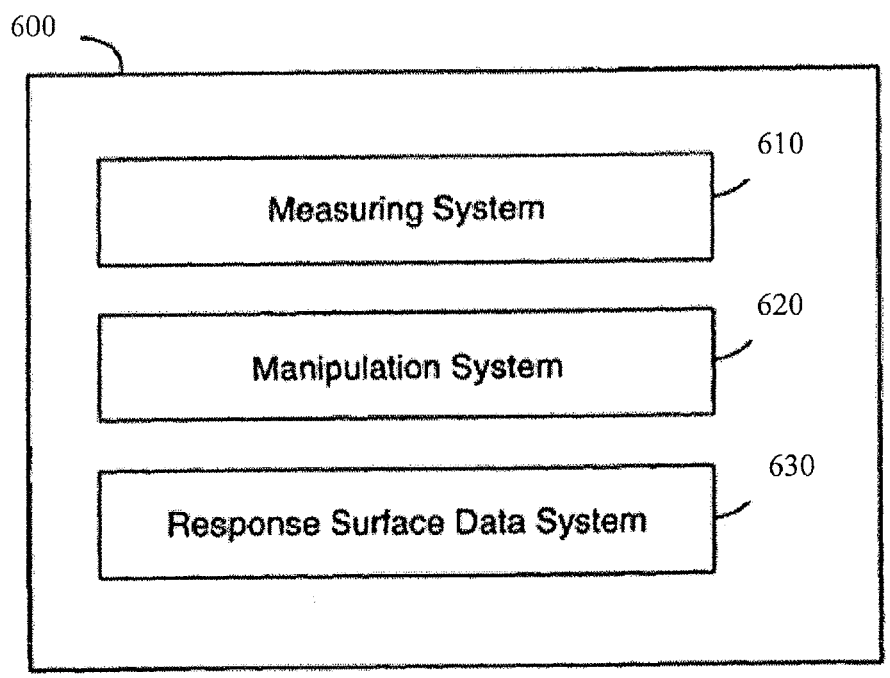
FIG. 6 depicts a block diagram of a system configured to provide response surfaces and/or use response surfaces for neural stimulation treatment planning in accordance with embodiments of the present disclosure.

FIG. 6 depicts a block diagram of a system configured to provide response surfaces and/or use response surfaces for neural stimulation treatment planning in accordance with embodiments of the present disclosure. Consistent with various embodiments of the present disclosure, the system 600 can be configured to implement the algorithms (e.g., 500) described herein. The system 600 includes a measuring system 610 for determining an initial state of the inflammatory system through surrogate variables. Suitable examples of measuring systems 610 include, but are not necessarily limited to, the heart rate, which can be determined through pulse oximetry.

If the desired final state of the inflammatory system requires large changes in the state variables selected, the change may be divided into several smaller incremental changes. The change to the incremental or final position, determined by the measuring system 610, may then be referenced to the appropriate response surfaces and therapy beyond neural stimulation, which may be prescribed, such as complementary music therapy.

A manipulation system 620 can be used to alter the inflammatory system to reach the desired state. A few examples of manipulation system 620 include an electrical current generator combined with an electrode, an electrode support appliance and the patient reference electrode.

Consistent with one embodiment, a response surface data system 630 can use a mathematical relationship between the initial state of the inflammatory system (as the state of the surrogate variables used to represent its state) and the desired state to generate response surfaces. Consistent with other embodiments, the response surface data system 630 can use an empirically derived relationship. The empirically derived relationship can be developed individually for each patient or based upon an average of the population, where only partial validation tests are used to verify that the individual response surface fits the population response inside a one sigma deviation. If the individual response is outside the one sigma expectation, then the individual experimentally derived empirical response surface could be utilized. The response surface system 630 can generate the response surfaces as part of the system 600, or the response surfaces can be provided as a data set to the response surface system 630 in an alternate embodiment. Various aspects of this disclosure may be implemented in software, firmware, hardware or some combination thereof.

Figure 7:
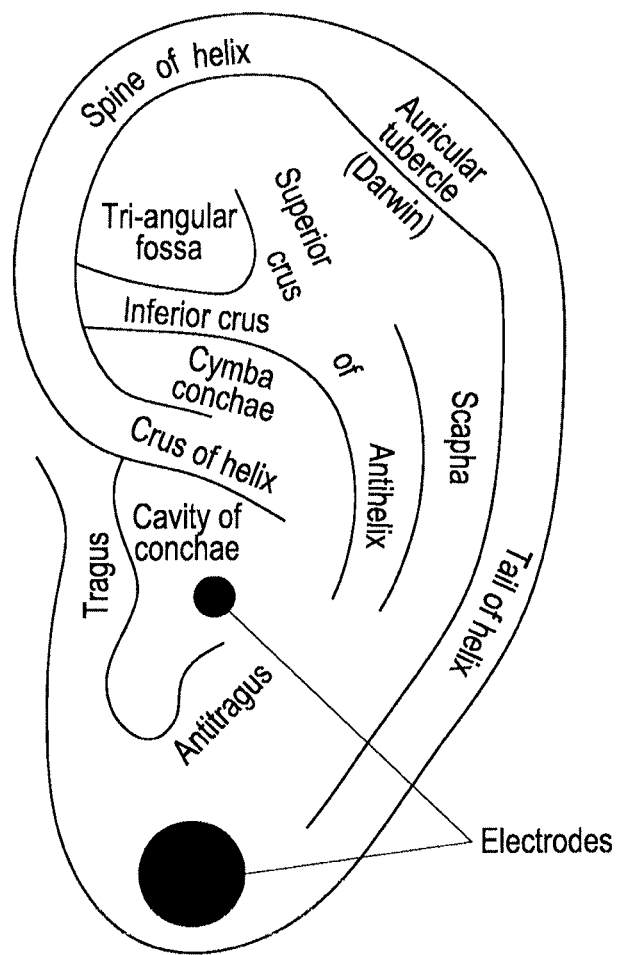
FIG. 7 depicts electrode placements within a patient's ear, consistent with embodiments of the present disclosure.

FIG. 7 depicts electrode placements within a patient's ear, consistent with embodiments of the present disclosure. The two solid circles show potential placements for stimulation electrodes within an ear. The upper, smaller circle can represent a potential placement for an electrode that delivers stimulation. The lower, larger circle represents a placement for a reference electrode. For instance, the effectiveness of the stimulation electrode can be significantly reduced if a good electrical contact is not first obtained between the stimulation electrode and the ear. The impedance between the two electrodes can be used to detect problems with this electrical contact.

Figure 8:
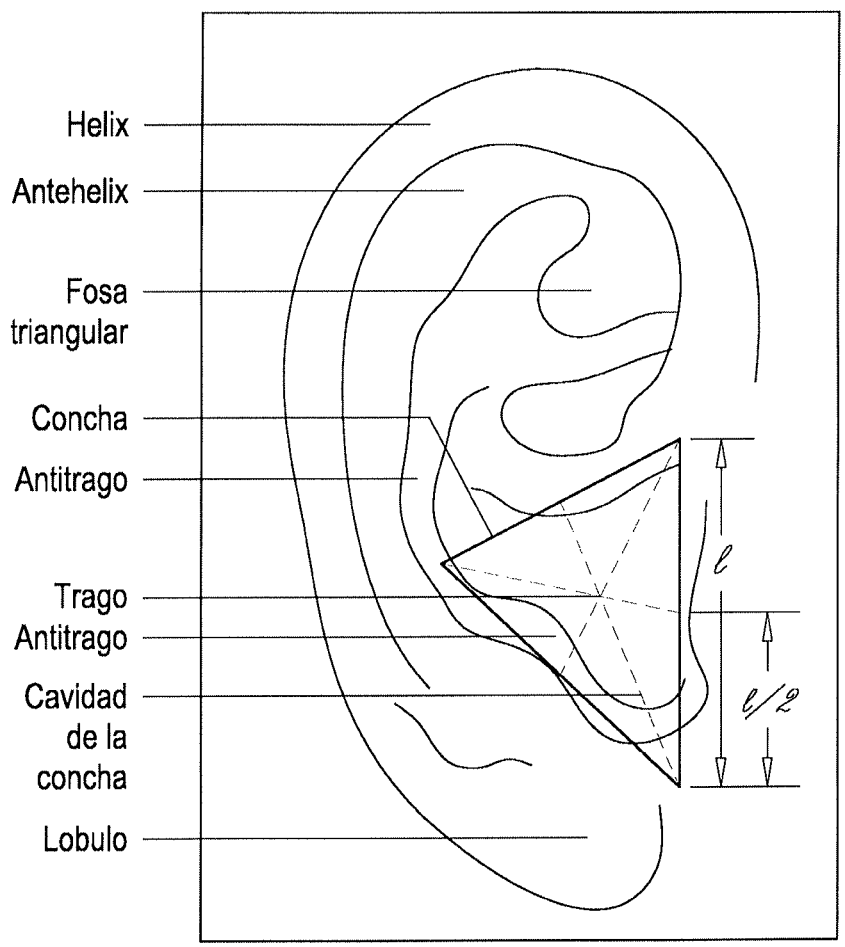
FIG. 8 depicts a diagram for identification of a stimulation location in a patient's ear, consistent with embodiments of the present disclosure.

FIG. 8 depicts a diagram for identification of a stimulation location in a patient's ear, consistent with embodiments of the present disclosure. Three data points are identified and used to form a virtual triangle. The (center of the) triangle is then used to identify a stimulation location. For instance, each edge of the triangle has a respective length (1). The intersection of lines connecting a distal corner of the triangle to the midpoint of an edge can be used to identify the stimulation location. Another fact can include the angle from the horizontal of the actual location of the stimulation site with regards to the ideal site, with zero degrees corresponding to the front of the patient and increasing to 360 degrees in a clockwise rotation. Other methods and algorithms can also be used to identify a possible stimulation point. For instance, additional points on the ear can be identified and used to further refine the location of the stimulation point.

Figure 9:
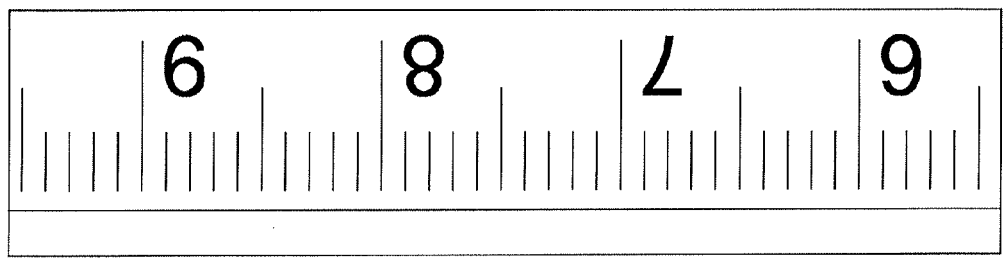
FIG. 9 depicts the front side of two earpiece structures having a plurality of electrodes, consistent with embodiments of the present disclosure.
Figure 9:
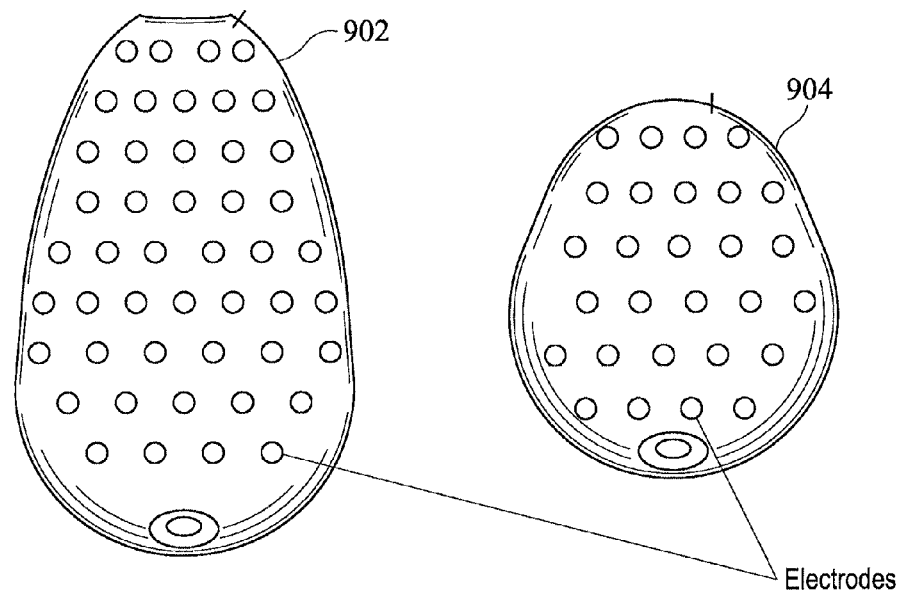

FIG. 9 depicts the front side of two earpiece structures 902 and 904 having a plurality of electrodes, consistent with embodiments of the present disclosure. The two earpieces have different shapes, which provide different fits for a potential user. The fit of each earpiece can be particularly relevant for electrode placement, comfort, maintenance of good electrode contact with the skin and/or other considerations. The use of an array of multiple electrodes can be particularly useful for a variety of reasons.

Such earpiece structures can be manufactured using a variety of housing or encasings (and other known technologies and techniques) for containing the circuits and related elements in proximity of the auricular regions as described above (e.g., in connection with the Figures). As examples, earpiece structures can be customized to a particular wearer's ear and/or manufactured in large batches using silicon or plastic. This allows for mechanical strength and support, formable structures, and also allows for placement of various electrodes within the earpiece structure. Such earpiece structures can also be manufactured (optionally with a protective layer against ear-wax) using a variety of manufacturing processes. For further discussion and details relating thereto, reference may be made to U.S. Patent Documents identified by U.S. Pat. No. 7,471,800 (e.g., FIG. 1), and U.S. Pat. No. 8,412,100 (e.g., FIG. 14). Each of these patent documents is fully incorporated herein by reference for such related teachings and more particularly, with regards to manufacturing of protective layers, earpiece housings, housing materials, and placement of elements therein.

In a first instance, a particular electrode from the array of electrodes can be selected to provide the stimulation. A first selection parameter can be the location of the electrode within the ear. A control switch (either in the remote stimulation generation circuit or within the earpiece) can selectively apply the stimulation signal to a particular electrode that corresponds to a desired location. In certain instances, this selection can be made using anatomical measurements of a particular patient, which can be correlated to predetermined categories of patients having similar measurements. In some instances, a training phase can be implemented during which different electrodes are tested and feedback is used to select an appropriate electrode for subsequent stimulation. Still other instances allow for dynamic changes to which electrode(s) are used for stimulation. For example, an impedance measurement may indicate that a particular electrode has lost (or reduced) electrical contact with the patient (e.g., due to movement by the patient). In another example, a stimulation profile may change the location of the stimulation during a stimulation sequence.

Other aspects of the present disclosure recognize that multiple electrodes can be used during a particular stimulation sequence/profile. For instance, a stimulation signal can be provided to several electrodes at the same time. This can be particularly useful for providing the stimulation signal over a larger area. In another instance, different stimulation signals can be provided to several electrodes at the same time. This can include, but is not necessarily limited to, bipolar stimulation signals between two electrodes.

The particular embodiment depicted in FIG. 9 shows 31 electrodes distributed in the region where it is desired to obtain the response surface. Electrode support appliances with more or less electrodes could be used in various embodiments. Moreover, different patterns for the electrode placement and/or different electrode shapes are also possible. In certain embodiments, the multiple electrode appliance could be used (only) in an initial visit to select a standard single electrode appliance from a catalog of available appliances. The selected electrode appliance can then be provided for chronic use for the particular patient, with the single electrode appliances being of lower cost than a multiple electrode appliance and/or having increased reliability due to the smaller number of failure points, this approach will not only decrease the cost per use but the reliability of the system overall.

Figure 10:
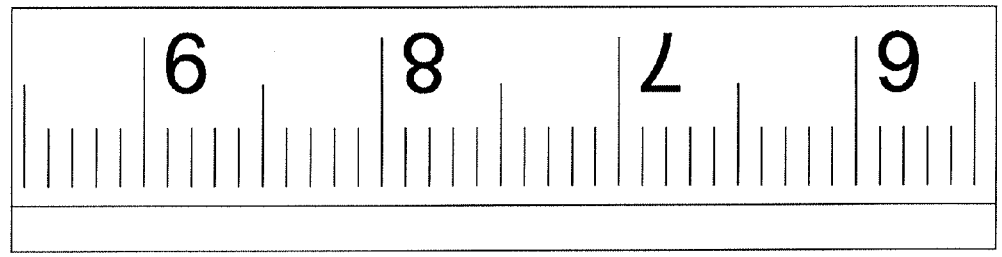
FIG. 10 depicts the back side of the electrode support structures, consistent with embodiments of the present disclosure.
Figure 10:
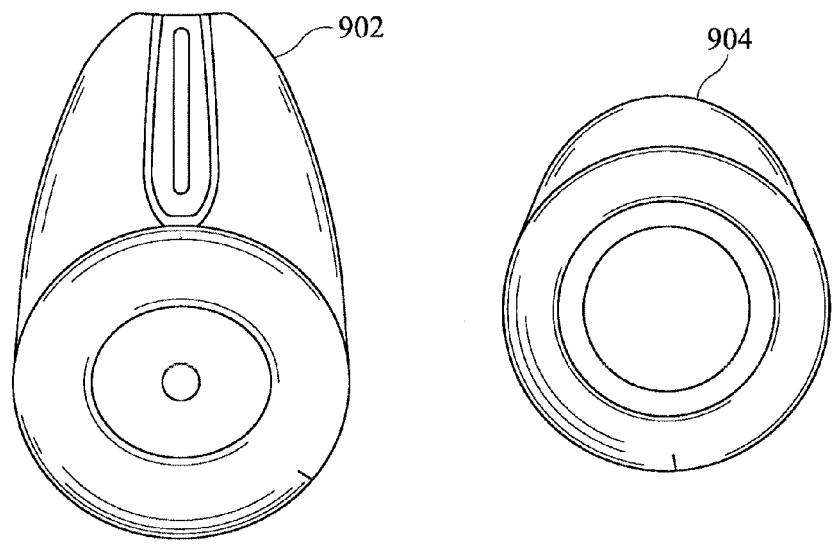

FIG. 10 depicts the back side of the electrode support structures 902 and 904, consistent with embodiments of the present disclosure. The hollow area of the structures can be used to present electrical connection wires to the electrodes. In certain embodiments, the hollow area can also contain electrical circuitry, e.g., for switching and/or control of electrical signals. This hollow area can also be used to send audio information in the form of air pressure waves to the tympanum of the patient. In one embodiment, the audio information can be used to restore normal hearing despite the obstruction produced by the electrode support appliances. In another embodiment, the audio information replaces a hearing aid appliance. In still another embodiment, the audio channel can be used to channel audio from a cell phone, MP3 player TV, DVD, or Bluetooth or any other transmission protocol audio information. In still another embodiment, this audio channel can be used to complement and/or supplement the stimulation therapy with music therapy to induce relaxation and activation of the parasympathetic system. In still another embodiment, a voice-activated fully-functional cellular phone or radio communications device could be included in the system and attached to the earpiece and electrode support structure.

The particular shape of the support structures are provided as examples of two possible shapes, and are not meant to be limiting. In certain embodiments, the material used for the electrode support appliances can be silicon based; however, other materials are also possible.

Figure 11:
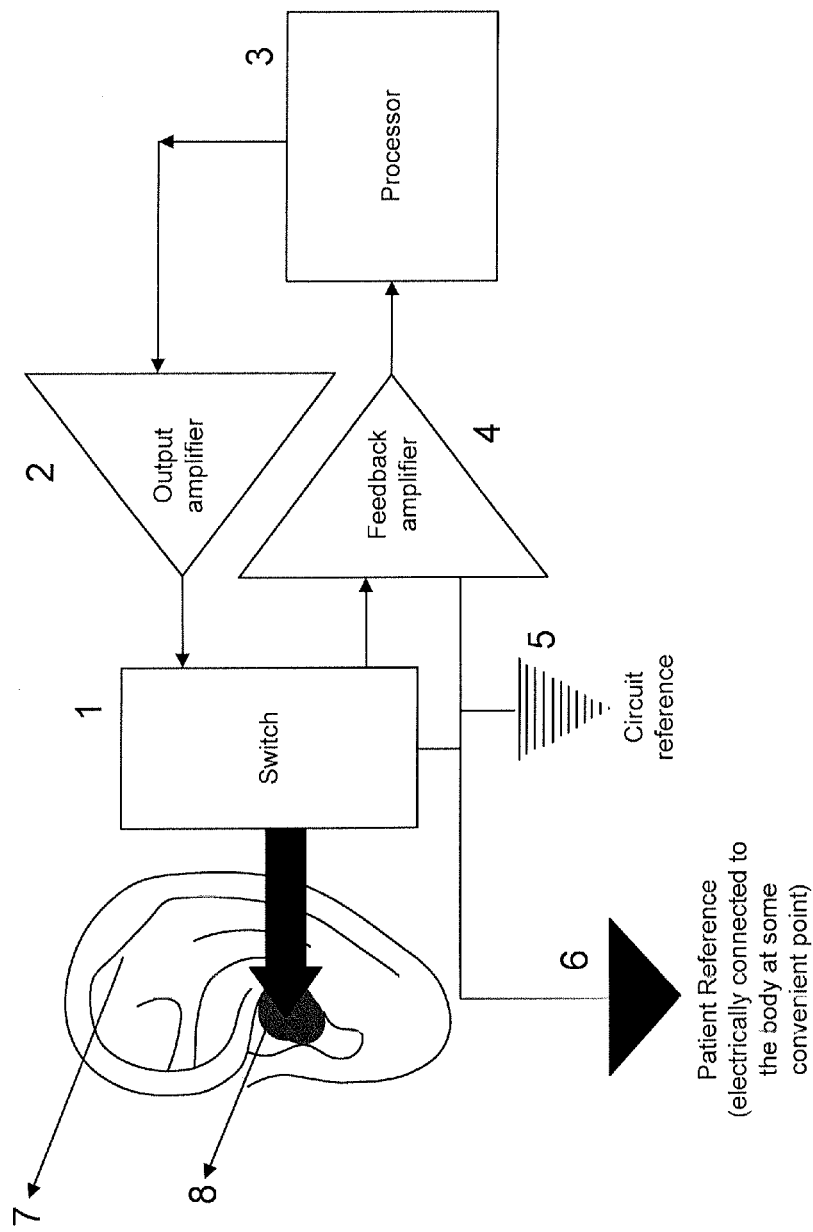
FIG. 11 depicts a functional diagram of a stimulation system, consistent with embodiments of the present disclosure.

FIG. 11 depicts a functional diagram of a stimulation system, consistent with embodiments of the present disclosure. Item 8 is the electrode support appliance; 7 is the ear of the patient being stimulated; 6 is the patient reference, connected to a convenient location near the stimulation site, but distal to it, for instance, connected to the inferior ear lobe; 5 is the circuit reference ground; 4 is a feedback/amplifier; 3 is a processing system where the data is analyzed and decisions are made; 2 is the output amplifier that generates the stimulation current; 1 is a switch that can connect the output amplifier to particular electrodes of an array of stimulation electrodes.

Consistent with embodiments of the present disclosure, a stimulation profile can be generated by first performing a testing procedure. A non-limiting example of a procedure is provided as follows. Once the circuit is powered, under the control of the processor, each electrode is stimulated in sequence for a programmed period of time (1 to 10 minutes) for each electrode and the heart rate and/or the heart rate variability is calculated for each electrode. Information from this procedure can be used in connection with an empirical response surface. This can include the use of the processor depicted in the system or of an externally-provided processor that receives data from the procedure. For instance, a device not shown in the Figure can communicate with the system through a standard based or proprietary protocol—e.g., Bluetooth, Wi-Fi or USB. This response surface can then be used to decide which electrode from the support appliance can be used to obtain the desired change in the inflammatory system.

Consistent with embodiments of the present disclosure, a first system can be designed for use in such test procedures. Thereafter, a second system can be used to deliver the therapeutic stimulation. For instance, the first system can include a support structure/earpiece with many different electrodes, sensors and other feedback mechanisms. Thus, the testing procedure can incorporate a number of different factors, inputs and feedback. Thereafter, a particular system can be selected using the results of the testing procedure. This second system can be a simplified version of the system used for testing, which can be particularly useful for reduced cost, increased reliability and/or portability, among other possible advantages. For instance, the second system can reduce or remove the number of sensors and feedback mechanisms. In other instances, the number of selectable electrodes can be reduced. Another possibility is the use of less powerful processor(s) and predefined earpiece shapes. In some embodiments the response surface obtained may indicate that a custom-made cast should be made of the patient's ear to be able to create a custom electrode support appliance to be able to obtain the desired response.

Consistent with certain embodiments, one or more of an ECG, temperature, Oxymmetry, HRV and pressure sensors could be left in the second device. This can be useful for allowing a physician to monitor the patient during the subsequent stimulation procedures, either locally or remotely though the Internet or other networked data system. For instance, an oxymeter (e.g., using an oxygen sensor that is located in the inferior ear lobe) can be used to obtain the heart rate and the heart rate variability and/or an ECG measurement could be used. The final device could be used and operated by the patient or a nurse assistant.

Figure 12:
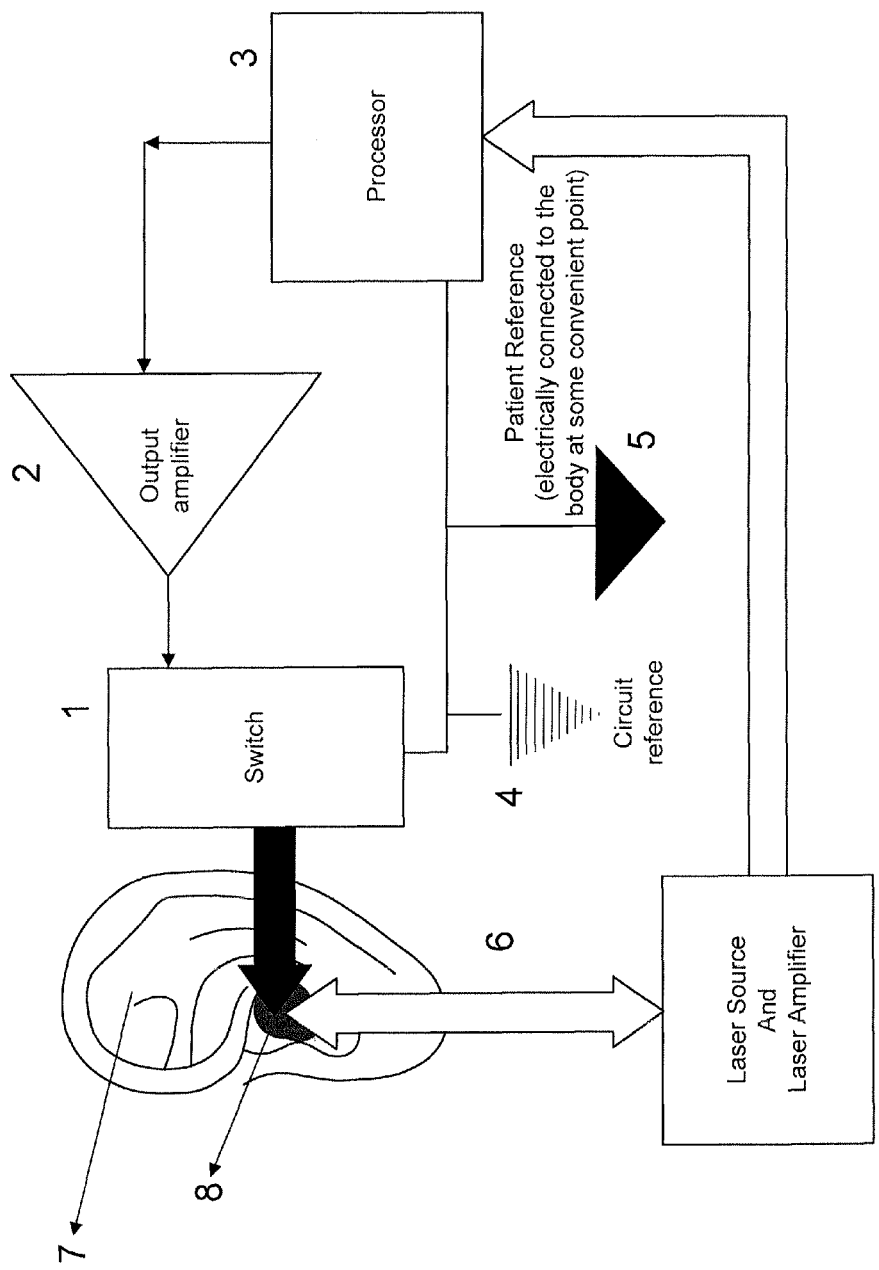
FIG. 12 depicts a system using a temperature sensor, consistent with embodiments of the present disclosure.

FIG. 12 depicts a system using temperature sensor, consistent with embodiments of the present disclosure. Consistent with embodiments of the present disclosure, a temperature sensor can be used to provide feedback relative to stimulation profile(s). For instance, a laser temperature sensor can be used to detect the small temperature changes that can indicate a change in the parasympathetic to sympathetic balance, which will create a surrogate variable to assess the changes effected by the stimulation upon the inflammatory system.

Figure 13:
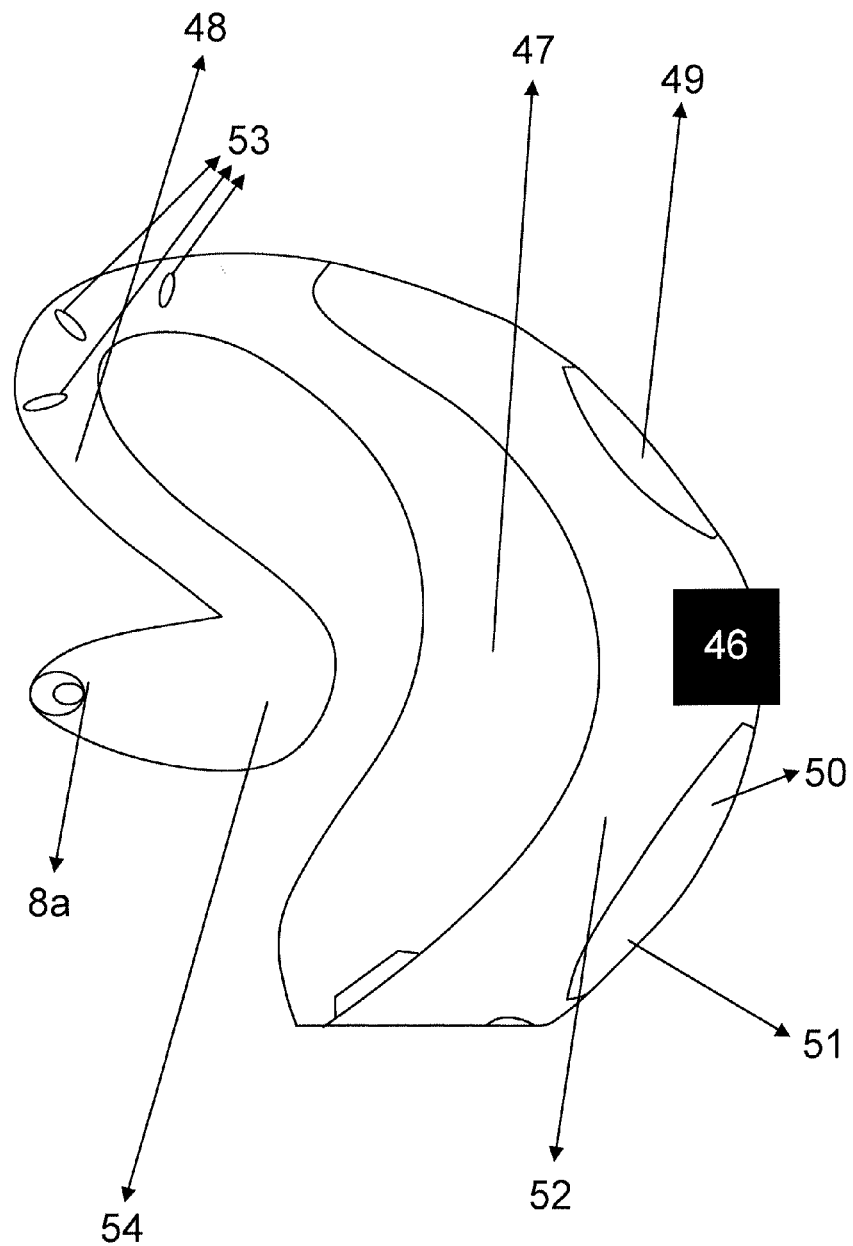
FIG. 13 depicts an implementation of a stimulation device, consistent with embodiments of the present disclosure.

FIG. 13 depicts an implementation of a stimulation device, consistent with embodiments of the present disclosure. The device 46 of FIG. 13 can be used in the physician's office. A corresponding patient-operated device can also be provided with a similar, but reduced, set of features, e.g., without the switching control and wiring and with simpler processing circuitry. 8a represents the electrode support appliance/earpiece. 54 is an interface to the support appliance 8a. 48 is the hollow duct that has the wires and the air duct to send the audio waves to the ear of the patient. 53 are pressure equalization holes to accommodate atmospheric pressure changes. 47 and 52 house the electronics and the power source (e.g., a rechargeable battery) of the device. 49, 50 and 51 show buttons that can be used to control the operation of the device.

Various embodiments of the present disclosure are directed toward acquiring data from the various sensors and to providing the data for analysis by a patient or health care specialist. For instance, ECG data can be acquired from sensors and analyzed by a processing system. A data interface can be used to upload the ECG data to a remote device. A patient or health care specialist can then review the data. This reviewed data can be used in developing a treatment plan, which can include additional treatment options (e.g., selecting medication or changing medication dosage), and/or adjustments to the stimulation provided by the stimulation system. Information other than, or in addition to, ECG data can also be acquired and uploaded.

Certain embodiments contemplate a wired interface for uploading the information. The interface can include one or more standardized interfaces (e.g., USB or Firewire) or proprietary interfaces. For example, the system can include a USB circuit that is configured to operate as a USB peripheral device. A USB cable, with USB connectors, can connect the system to a remote processing device (e.g., a laptop computer, tablet computer or personal computer). The acquired data can be automatically uploaded using software drivers and/or the system can appear as a storage device (e.g., flash drive) upon which the acquired data is stored.

Various embodiments are directed toward a wireless interface for uploading of the acquired data. The wireless interface can be configured for use with various standardized protocols (e.g., Bluetooth, Wi-Fi/IEEE 802.11xx, cellular protocols, near field communications or WiMax). In certain embodiments, the wireless circuit for the interface can be configured to conserve power by powering down or entering a low power state between uploading.

Consistent with one or more embodiments, access to the acquired data can be limited to authorized persons. This can include, for example, the use of encrypted communications and/or password protection.

Figure 14:
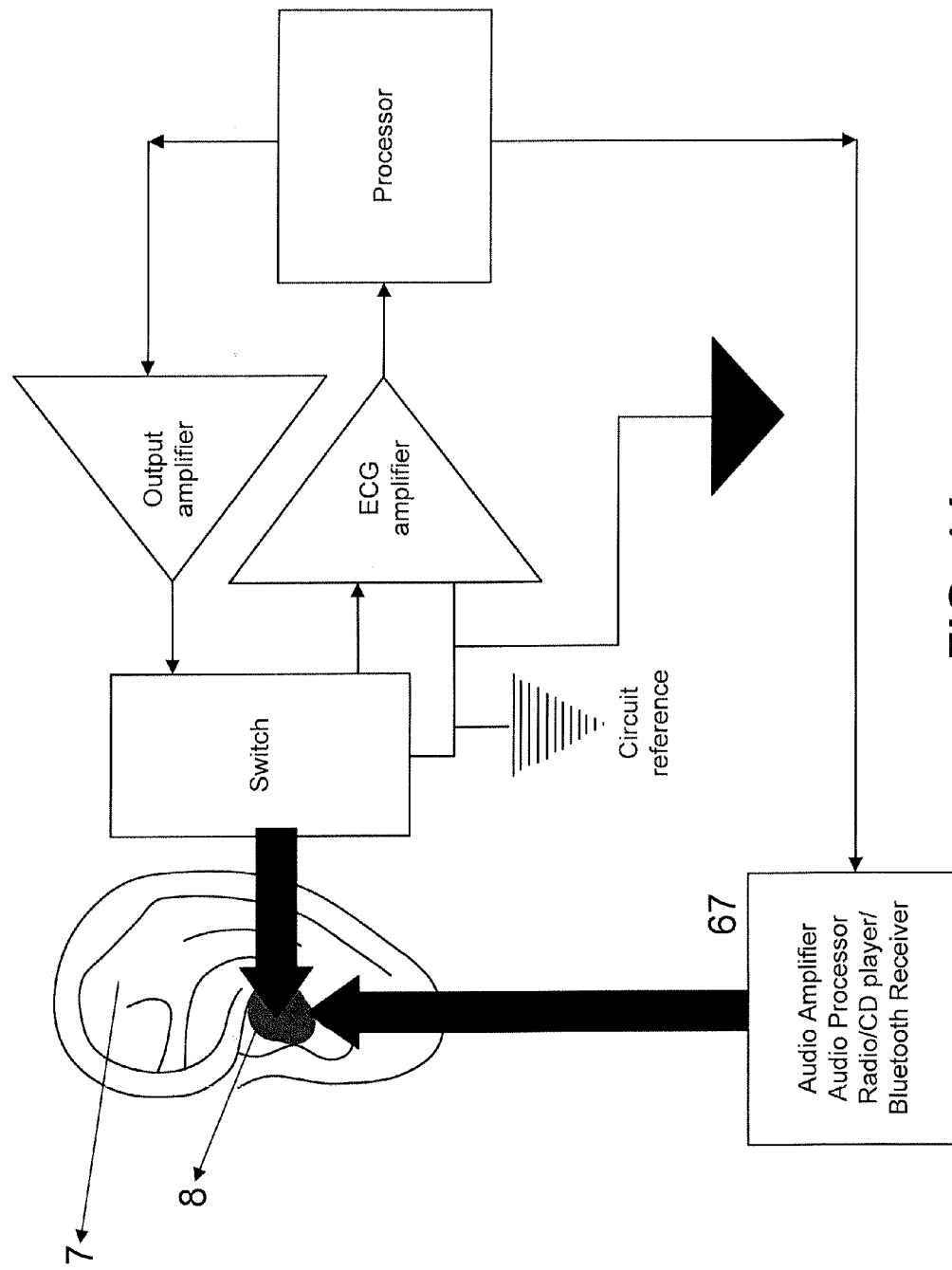
FIG. 14 depicts an implementation of a device having an audio amplifier and transducer, consistent with embodiments of the present disclosure.

FIG. 14 depicts an implementation of a device having an audio amplifier and transducer, consistent with embodiments of the present disclosure. Audio amplifier/transducer 67 is provided to deliver audible sounds to a patient. Placement of the earpiece can adversely impact a patient's hearing by reducing/blocking external sounds. Accordingly, audio amplifier/transducer 67 can reproduce/amplify such external sounds. An external microphone can detect and provide such external sounds to the amplifier/transducer 67. This can be particularly useful for restoring the patient's normal hearing during therapy. In other embodiments, the device can function as a hearing aid. Still other embodiments contemplate the delivery of audio from electronic devices, such as a cell phone earphone through Bluetooth or other wireless standard, audio from a CD/DVD or TV set and/or computer and/or music therapy generator and/or other audio sources. The implementation is shown with an ECG feedback but it could be used with other feedback variables (e.g., laser temperature sensor, pressure sensor, indirect pressure sensor, ECG amplifier and/or oximeter pulse detector). The final patient device can have all these components, but a simpler circuitry and a one or two electrode support appliance.

Figure 15:
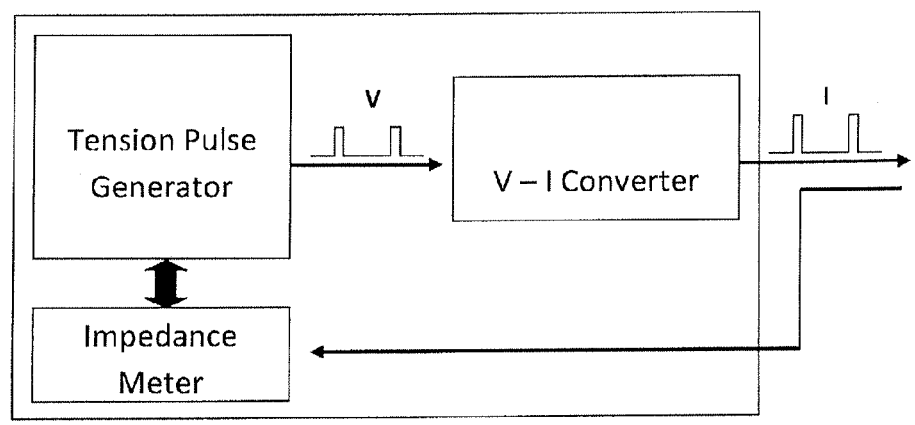
FIG. 15 shows an example block diagram of a device designed to obtain the required stimulation parameters, and access inter-electrode impedance.

FIG. 15 shows an example block diagram of device designed to obtain the required stimulation parameters, and access inter-electrode impedance. Such an apparatus includes a tension pulse generator, a voltage-current converter, and an impedance meter. The tension pulse generator applies voltage pulses to the voltage-current converter, which converts the voltage into current. The current pulses are applied to an electrode, which feeds back the impedance level to the impedance meter. The impedance meter can adjust the tension pulse generator based on the measured value. Various other input variables are also possible, either separately or in combination with those variables expressly mentioned herein.

Figure 16:
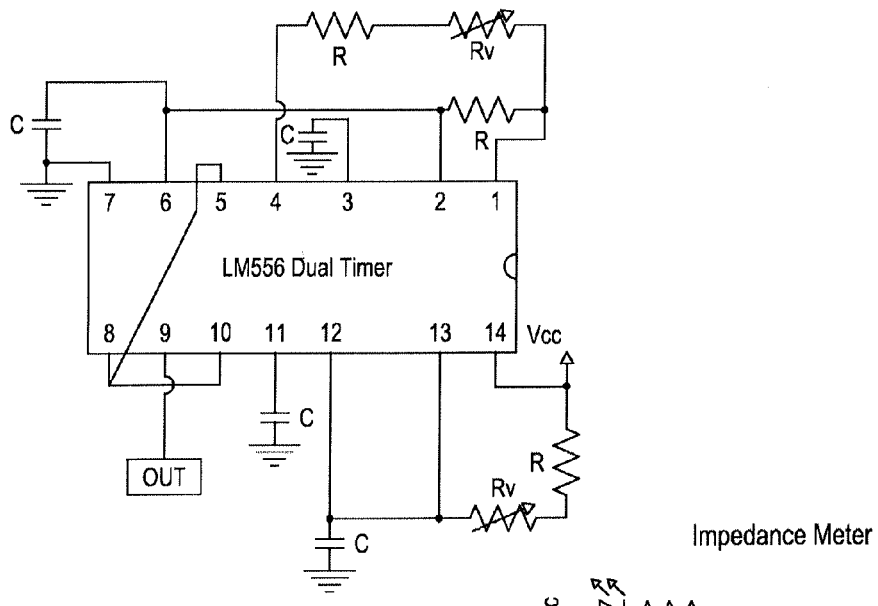
FIG. 16 shows an example illustration of circuit diagrams, consistent with embodiments of the present disclosure.
Figure 16:
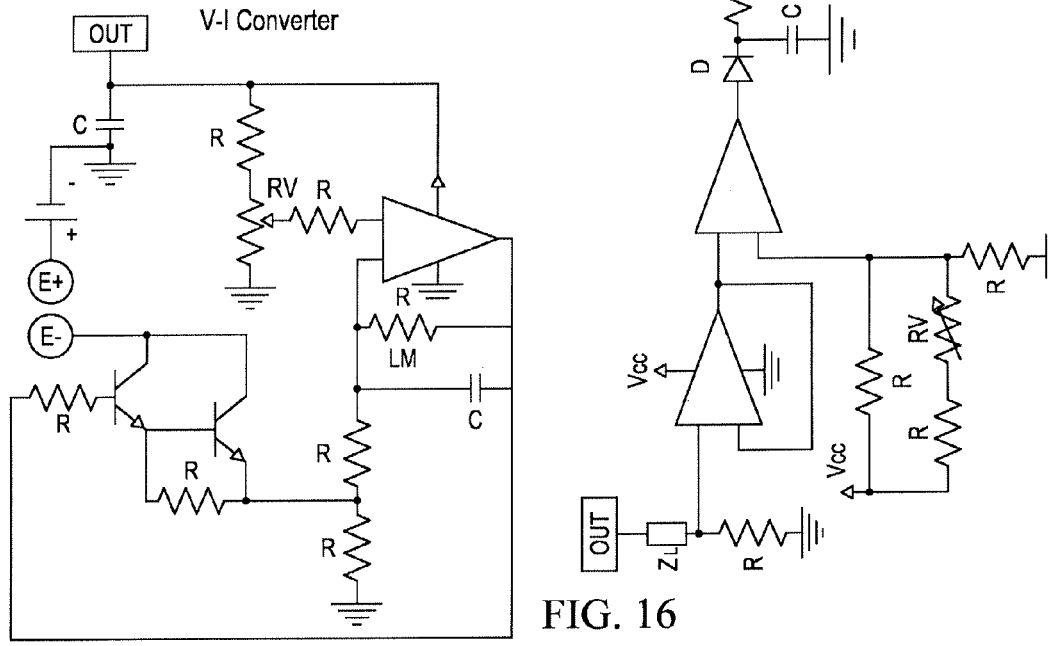

FIG. 16 shows an example illustration of circuit diagrams, consistent with embodiments of the present disclosure. The circuit diagrams provide example circuits for use in connection with each of a tension pulse generator, a voltage-current converter, and an impedance meter.

A number of experimental tests, devices and procedures were implemented in accordance with aspects of the present disclosure. The following discussion includes a non-limiting description of such experimental aspects.

For the purpose of the experimental discussion, treatment of arterial hypertension was targeted; however, by treating the inflammatory process, aspects of the instant disclosure are also directed toward improved treatment of other diseases that are also affected by the inflammatory process.

Without being limited in theory, it is believed that the stress cycle of humans can enter into a positive feedback loop such that stress generates more stress. The increase in stress may be associated with (if not triggered by) the flight or fight response mechanisms, whereby the sympathetic system becomes activated and often suppresses the activation of the parasympathetic mechanisms. The positive feedback loop of stress, for example, can be seen in the opposite case of exercise. Regular exercise can aid in the treatment of many diseases, even in advanced heart failure, because it produces a paradoxical rebound of the parasympathetic system activation post-exercise. Furthermore, the rebound of the parasympathetic system is known to last for 48 hours as the parasympathetic system remains activated. The rebound of the parasympathetic system lasting for 48 hours supports the idea that interval exercise is more effective in helping with cardiovascular diseases than continuous exercise.

The effectiveness of interval stimulation sessions (3 times per week, 15 minutes per session) was evaluated after one month of continuous treatment. The interval sessions aim to break the continuous sympathetic activation produced by the flight or fight response or "stresses" of regular life in order to break the positive feedback loop that has been created and allow the sympathetic system to return to a more balanced point. The interruption of this positive feedback loop created by the constant activation of the sympathetic system can be achieved by trial-and-error with multiple combinations of treatment frequency and duration until the optimum duration and frequency is determined. The optimum duration and frequency can be varied and advanced based on the individual patient characteristics and pathology being treated.

The vagal system is believed to be critical to the workings of the parasympathetic system. Therefore, aspects of the present disclosure are directed toward stimulation of the auricular nerve to activate the parasympathetic system. Further, the activity of the vagal system has been linked to the inflammatory response system. As a result, activation of the vagal system is believed to be influential in stopping the inflammatory process. For example, the importance of the vagal system has been shown to stop the gangrene processes in the legs of frogs by direct stimulation of the vagus nerve at the level of the neck. Given the association between the nervous and the immune systems, a treatment system that reliably influences this association in a positive manner can improve the course of diseases in which the inflammatory system is a cause for progression. Furthermore, the activation of the parasympathetic system is believed to be associated with ameliorating the excessive response of the neural control system of the heart during periods of acute stress, like those that occur during heart failure or ischemic episodes. For instance, evidence suggests that activation of the parasympathetic system can reduce the size of a myocardial infarction by 70% or more and that it can decrease mortality by a similar percentage. Similar effects have been shown in models of heart failure.

Methods, apparatuses, and systems, consistent with the instant disclosure, were tested in patients with chronic hypertension currently being treated with drugs. Chronic pressure maps were constructed before and after treatment. The results showed that some patients were actually hypertensive, as indicated by the pressure maps before the treatment, while the other patients' hypertensivity was being controlled successfully by the drugs. After the treatment, none of the patients were hypertensive (per the post-treatment pressure maps). Further, no ill effects or side effects were reported by any of the patients studied. These results suggest a consistent methodology for applying auricular nerve vagal stimulation, with an extremely low cost benefit ratio. Moreover, one of the patients who had Tinnitus reported that the buzzing sound was partially gone after only one session of the therapy.

In order to accurately locate and stimulate the auricular branch of the vagus nerve, the anatomical organization thereof was investigated. The anatomical aspects include: auricular branch of vagus nerve (ABVN); great auricular nerve (GAN); auricular temporal nerve (ATN); superficial temporal artery (STA); the lateral occipital nerve (LON); blood vessels (V). Acute measurements were made in patients that included evoked potentials, direct anatomic studies, and impedance measurements to define the exact region to be stimulated. These measurements, in combination with occidental and oriental information regarding acupuncture points, suggested a particular location of the stimulation point of the auricular branch of the vagus nerve.

In order to implement the auricular nerve stimulation, a pulse generator with variable frequency, pulse width, and amplitude was designed and used. This stimulator had two main modules: a pulse generator and a voltage/current converter. The battery supplied 27 volts to the device. Initial treatments were conducted at pulse repetition rate of 20 Hz, with a pulse width of 200 microseconds. Current was increased until it became uncomfortable for the patient, and then reduced to the highest level that remained comfortable for the patient. Patients would often fall asleep during the stimulation sessions.

The ear was cleaned with a cotton isopod and alcohol (or other acceptable cleaning agent) until the region was free of grease and wax, and the skin had been reddened. If the auricular device was not already pre-loaded with conductive gel, a generous amount of conductive gel was applied to the region of the auricular branch of the vagus nerve, and to the region of the reference electrode before positioning them.

In instances in which the patient was assisted by an operator in placing the auricular device, the operator measured the inter-electrode impedance, and confirmed that it was below the set threshold defined for the electrode system. The inter-electrode impedance can differ depending on the geometrical properties of the patient and the auricular device. Once the desired low impedance was achieved, the stimulation amplitude was increased (by the operator or automatically) until the patient reported discomfort. The stimulation amplitude can then be decreased below that level, and then maintained.

The injection of low amplitude pulses of current facilitates the measurement of the ratio between the voltage applied and the current achieved between the reference electrode and the stimulation electrode. The voltage waveform was identical to the one used for stimulation to obtain accurate estimates of the complex impedance that exists between the electrodes. An example electrode arrangement, consistent with the disclosure, includes one 1-2 mm diameter silver electrode, and a large reference electrode (approximately 10 mm in diameter). Using a repetition rate of 20 Hz, a pulse width of 200 microseconds, and currents that ranged between 800 and 5,000 microamperes, the inter-electrode impedance was targeted at a value below 5,000 Ohms.

The electrodes for stimulation the auricular branch of the vagus nerve (ABV) were of a monopolar configuration. The electrode system also included a reference electrode of 10 mm in diameter that can be placed in the inferior region of the ear lobe. The ABV stimulation electrode was spherical in shape, and is approximately 1 to 3 mm in diameter. The exterior surface of the ABV stimulation electrode can be composed of silver (AG).

In order to effectively stimulate the auricular branch of the vagus nerve, the consistent placement of the ABV stimulation electrode can be an important component of effective stimulation. Accordingly, an ear-casting method has been developed in order to construct an electrode support system individualized to the anatomy of each patient. This can be particularly useful for the precise and comfortable systematic location of the electrode in a precise region for each therapy session.

An example embodiment of an ear-casting method includes the following aspects. First, a three-dimension copy of an ear of the individual to be treated is made by applying heavy silicone over the region of the external ear. This casting obtains a negative of the ear where the electrode can later be fixed. After the cast is hardened, it is removed from the ear of the patient. Next, the negative casting of the ear is covered with a thin layer of a lubricant (e.g., liquid Vaseline), and plaster (such as a heave silicone) is applied to the negative casting. The plaster is removed carefully in order to not damage the cast. Through this process, an individualized copy of the inside of the ear is created.

A (silver ABV) stimulation electrode can then be placed in the correct site based on anatomical properties of the individual. For instance, by identifying three triangle-forming points on the ear, the correct placement is found at the region of intersection of three medial lines that go from each of its vertices to the middle of the opposing side. The stimulation electrode can then be centered in this region. This placement can be carried out using a small incision (equivalent to the size of the electrode) in the cast. The electrode is placed and fixed to the cast with instant glue (to avoid any undesired movement during the final casting process). A lubricant is again applied to the plaster cast to create the final support for a wash of light silicone that will support the electrodes inside the ear of the patient. After the silicone is dry, it is removed from the plaster cast, and the edges that do not form part of the earpiece are trimmed to ensure that the structure will fit perfectly inside the ear of the individual patient To determine the point where the electrode will be located in the plaster cast, a triangle can be traced in the mold of the ear. The placement of the electrodes corresponds to the final positions of that the electrode in the ear an individual patient. As a particular example, a triangle can be formed from points corresponding to a line of the branch or root of the helix, and passing with the other two sides by the trago and antitrago. The center point of the triangle (where the electrode will be placed) is found by drawing the three medial lines from the vertices to the middle of the opposing sides.

In placing the electrodes, it can be helpful to eliminate any deposits (dirt, grease, wax) on the electrodes to ensure accurate stimulation and firm placement. Therefore, the electrode is cleaned with, for example, a piece of cotton wet with alcohol. The regions of the ear that the electrodes will be placed are also cleaned.

Prior to placing the electrode support system, which includes the ABV electrode, in the ear, a layer of conductive gel is applied over the ABV electrode in order to reduce the impedance of the skin-electrode interface, and eliminate the discomfort level by facilitating the passage of current through the skin with low applied voltages (low impedance). This can facilitate a therapeutic level of therapy to be delivered to the ABV nerve. It can also be important to introduce the cast into the ear with care to not distribute the conductive gel so that the gel only ends up in the region where the ABV stimulation electrode will contact the skin. The reference electrode can be place in the inferior region of the ear lobe and is also covered with a layer of conductive gel over on the surface that is in contact with the skin.

Prior to stimulation of the ABV nerve, the correct placement of the electrodes can be verified. To accomplish this, an impedance meter is built can be included in methods and apparatuses of the instant disclosure. For example, an impendence meter can be built into the support structure described above. The inter-electrode impedance is determined using the same parameters for the applied voltage (frequency and pulse width) that can be used for stimulation. If the measured value is larger than a set value (e.g., 5,000 Ohms), the support structure (including the impendence meter) and the reference electrodes will be removed, and the placement process will be redone. Alternatively, a different stimulation electrode can be selected if an earpiece with an array of electrodes is being used. If after repeating the location process, an impedance value of less than 5,000 Ohms cannot be achieved, the electrodes and cast can be reconstructed. If the measured value is lower than 5,000 Ohms, the comfort level can be found, and stimulation can begin. The cast of the patient's ear can be created only once per patient; however, it can be recreated if the original cast is destructed or if the patient's anatomy changes.

Consistent with a particular experimental embodiment, the stimulation parameters were defined as: 20 Hz repetition rate of a single pulse of 200 microseconds pulse width and a current range between 800 to 5,000 microamperes. The actual stimulation parameters used can vary, including adjustments that are responsive to the patient's comfort level, tolerance, and the actual inter-electrode impedance.

After an inter-electrode impedance lower than 5,000 Ohms is achieved, the stimulating parameters of repetition frequency and pulse width were set. The current level was set to its minimum setting, and the stimulator was turned on. To establish the therapeutic current level, the current level injected was slowly increased until the patient starts feeling a slight discomfort in his external ear (similar to the feeling of a needle being lightly applied to the region). The current level was then decreased until the feeling was comfortable again for the duration of the therapy (approximately 15-30 minutes). The patient should feel the stimulation in external ear, and not in the ear lobe. If the patient feels the stimulation in the ear lobe, the placement of the electrodes step should be repeated, cleaning more intensely the external ear and being careful to not distribute the conductive gel when placing the support structure with the electrode into the ear.

Once all the parameters have been set correctly, the patient will be stimulated for 15 to 20 minutes for the hypertension clinical trials. The patient will be treated 3 times a week for 1 month. For other therapies, the frequency and duration of the therapy will be different. For instance, in the post myocardial infarction cases, the stimulation will be applied constantly from the time the patient experiences the infarct symptoms until the revascularization process is completed and the patient is stable according to his attending physician.

The parameters described were used for a single electrode embodiment. Other embodiments may use different parameters, e.g., depending on the exact geometry of the electrode arrays.

Figure 17:
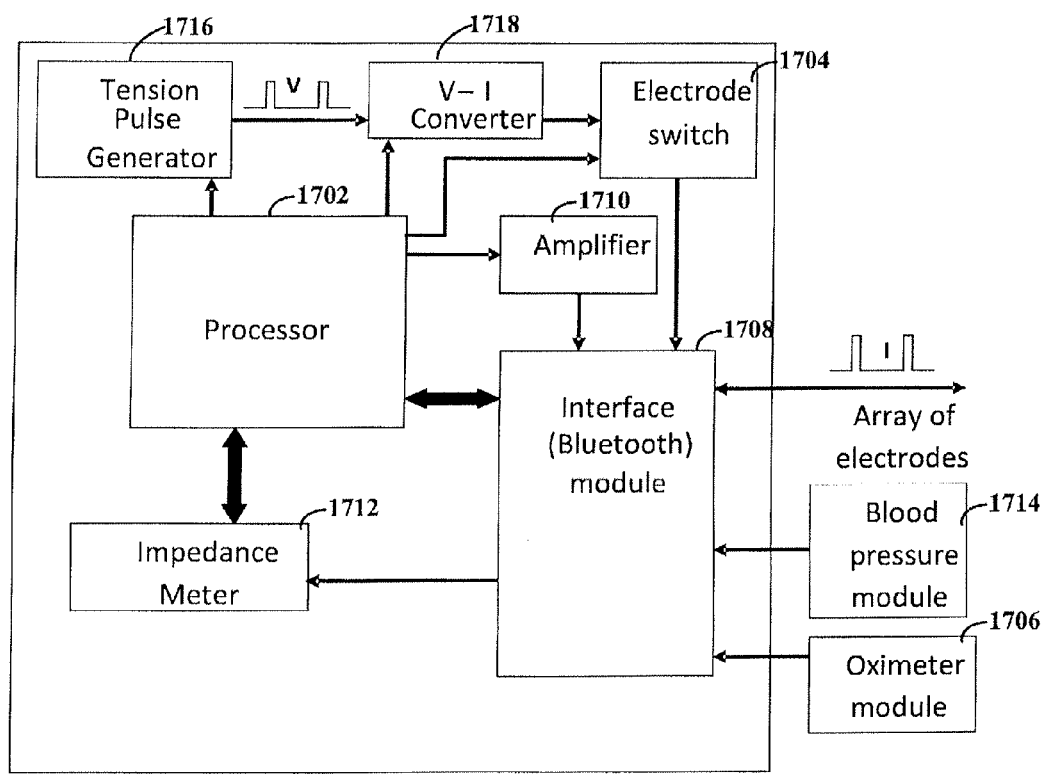
FIG. 17 depicts a block diagram of an apparatus and system for stimulation of the ABV nerve, consistent with embodiments of the present disclosure.

FIG. 17 depicts a block diagram of an apparatus and system for stimulation of the ABV nerve, consistent with embodiments of the present disclosure. The apparatus includes a processor 1702, which can make control decisions. The processor can include a microprocessor, a central processing unit (CPU) and/or specially-designed processing logic. Tension pulse generator 1716 can create electrical stimulation pulses. V-I converter 1718 can convert the electrical stimulation pulses from voltage to current.

An electrode switch 1704 can provide and direct stimulation current to different electrodes in a matrix of electrodes. The apparatus can also include input/feedback signals from, for example, a heart rate monitor 1706 (e.g., a pulse oximeter) or a blood pressure monitor 1714. The heart rate (HR) information is provided to the processor through an interface module 1708, which can be a wireless (e.g., Bluetooth) or a wired interface. The processor 1702 can toggle the switch 1704 to apply stimulation current to each electrode on the matrix for a set time (e.g., 1 to 5 minutes) and/or until a desired HR change is obtained. The HR change can be quantified and stored in memory.

Consistent with certain embodiments, the stimulation can be carried out using different electrodes in the array, and the electrode that produced the largest change in HR can be selected as the optimum electrode for that patient. A similar process could be used to determine the optimum individual parameters for pulse width, current amplitude and frequency of stimulation. This optimization can be carried out once per patient, and the patient specific information can be stored by the device and used thereafter. In other instances, the optimization can be carried out periodically (e.g., weekly) or in response to an input. The input could include, but is not necessarily limited to, a measured drop in the effectiveness of the treatment, such as less change in the HR or a user selection, such as pressing a reset switch.

Utilizing a multiple electrode array can help improve location-based accuracy, however, the cost of constructing such a device can also be higher. Moreover, the time to perform the initial optimization can also be increased. Accordingly, a multiple-electrode system may be deemed useful in more limited applications. One such use of this system can be for post-infarct cases. For example, where a patient has an infarct, the patient (e.g., in the ride to a hospital in an ambulance)

can be stimulated until the revascularization procedure is performed and thereafter, until the physician is comfortable that the patient is out of risk. The multiple electrode array apparatus described can allow for increased adaptability of the support structure. For example, this allows for the use of pre-constructed casts tailored to the most common anatomies (e.g., sizes small, medium, and large). Therefore, rather than delaying the onset of auricular stimulation to create the individual cast for the patient, the stimulation would be available immediately based on the optimization of the individual parameters available for multiple electrode arrays. The immediate availability of AVB stimulation can save the life of a patient that is at risk. The HR measurement module can communicate with the processor either directly or through some wireless protocol (e.g., Bluetooth, Wi-Fi). For this purpose, apparatus can have a Bluetooth module added that gets its input from an oximeter module with a pulse rate detector to measure the heart rate. The Bluetooth module has its counterpart connected to the processor.

For patients who need the chronic delivery of ABV therapy, an auricular stimulation device, consistent with the instant disclosure, could be combined with Bluetooth or wired earphones so that the patient could either talk on the phone or listen to music while receiving the therapy. For that purpose, apparatuses can additionally include a Bluetooth model, and an audio amplifier 1710. Moreover, for patients that need auditory amplification or earphones to be able to hear, the stimulator would be combined with the electronics of the earpiece. Additionally, musical patterns and even white noise can stimulate the parasympathetic system. Other embodiments can combine the stimulation of the auricular branch of the vagus nerve with a patient/physician-selected type of musical pattern or white noise that maximizes the parasympathetic effect. The processor 1702 can be configured to cycle through different musical/white noise patterns until the one that produces the largest decrease in HR is identified for a particular patient.

In other embodiments of apparatuses and methods, consistent with the instant disclosure, a direct or indirect estimate of the actual blood pressure can be obtained, and communicated through wires or wireless (i.e. Bluetooth) communications to a processor. The processor can be programmed to switch the electrodes used for stimulation until the electrode that creates a large decrease in arterial pressure is identified. Similarly, the stimulation current, frequency and pulse duration can be changed until the optimum effect is achieved.

Other embodiments can utilize heart rate variability estimates of parasympathetic/sympathetic balance. The analysis is accomplished by programming the processor, which determines what electrode/current level/frequency of stimulation and pulse width allows the device to achieve the optimum stimulation of the auricular branch of the vagus nerve.

In still another embodiment, the processor controls the automatic increase in stimulation current, triggered by the patient (in the case of self-administered therapy) or by the operator, until the patient sends a signal back to it (through a button wired or wireless) to indicate that the discomfort level has been reached. The processor will then send back the stimulation current amplitude by one step to stay at the highest stimulation level that is still comfortable for the patient.

Additionally, the processor can be programmed to allow for automatic measurement of the impedance 1712 between the stimulation and the reference electrodes. This measurement is reported back to the operator (or to the patient if the therapy is self-administered), and shows whether the electrode and its support material have been correctly placed, and the impedance is below a pre-established threshold for that electrode system. The correct impedance level can be shown through a set of Green/Yellow/Red LEDs, where the Green LED would indicate below-threshold impedance, the Yellow LED would indicate borderline impedance (e.g., near threshold), and the Red LED would indicate an above-threshold impedance.

Further, the processor can be programmed to continuously monitor the inter-electrode impedance during stimulation to ensure that the electrode skin interface has not changed. This monitoring is another mechanism that enhances the effectiveness of the therapy. In embodiments that include a processor programmed in this manner, an alarm can be placed with the support structure housing the electrodes to indicate that the impedance has exceeded the maximum threshold. The processor can additionally be programmed to report and calculate the number of therapy sessions where the impedance levels were not optimal. This can allow the operator and/or the patient to decide whether to repeat the session or not.

Figure 18A:
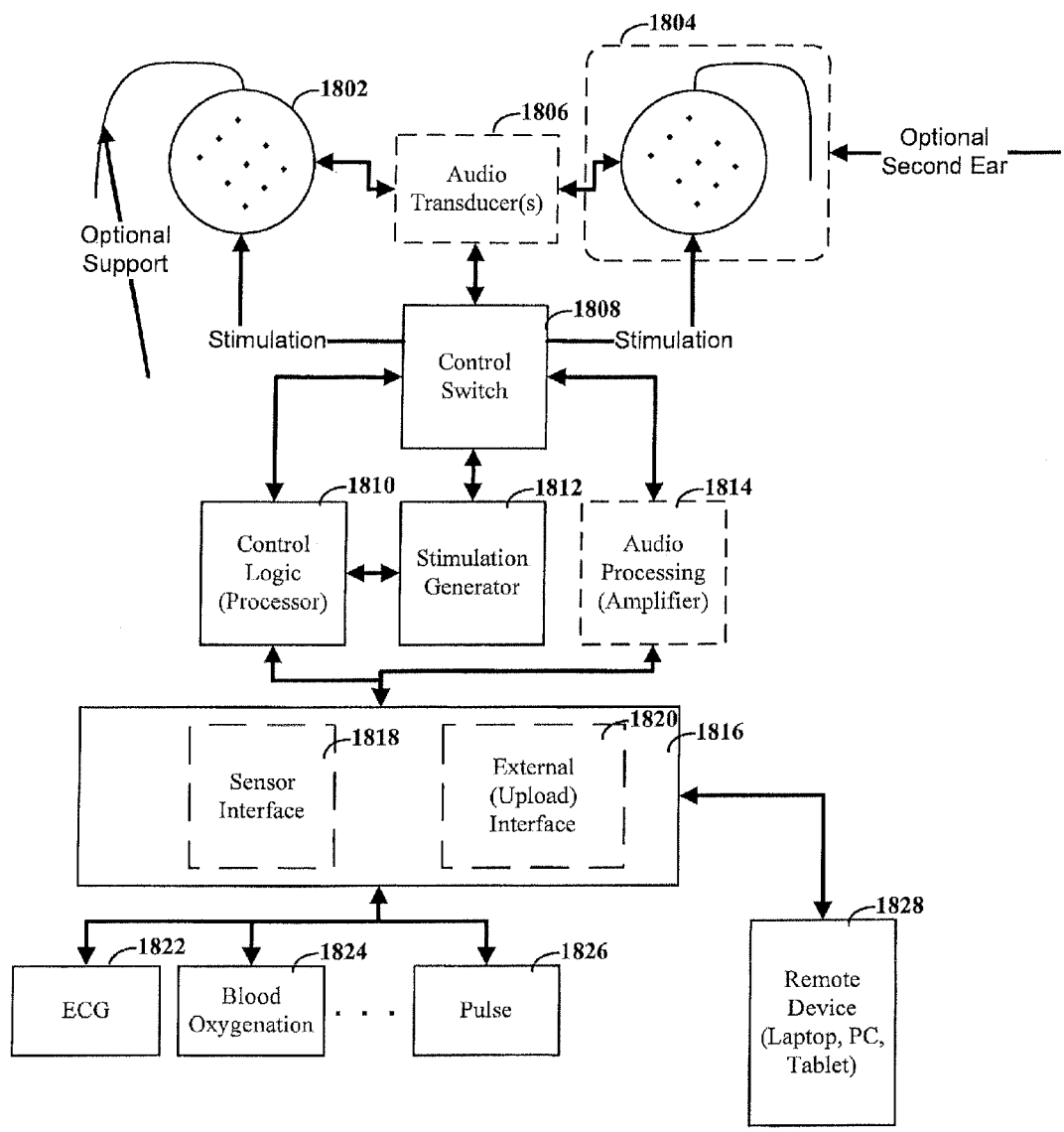
FIG. 18A depicts a block diagram of an apparatus and system for stimulation of the ABV nerve or nerves (in one or both ears) as may be useful for emergency situations by first responders, consistent with embodiments of the present disclosure.

FIG. 18A depicts a block diagram of an apparatus and system for stimulation of the ABV nerve or nerves (in one or both ears) as may be useful for emergency situations by first responders, consistent with embodiments of the present disclosure. The block diagram shows two different earpieces 1802, 1804. The second (optional) earpiece 1804 can be provided to allow for selective stimulation in one or both ears. The earpieces 1802, 1804 can include (optional) support structures that provide mechanical support for the earpieces (e.g., by being configured for placement behind an ear lobe). A particular application relates to the use of the apparatus and system in emergency situations, and will be discussed in more detail herein.

The use of two earpieces 1802, 1804 with respective stimulation electrodes allow for a variety of different applications and embodiments. For instance, it has been recognized that stimulation on each side of the body can be effective for reaching respective and different portions of the heart. Moreover, the portions of the heart that can be reached can vary from patient to patient. Accordingly, having the capability to stimulate from both sides of the body can be particularly useful for parasympathetically innervated regions of the heart. Consistent with certain embodiments of the present disclosure, a particular side can be selected for stimulation in response to the desired stimulation location of the heart. In some embodiments, such as in the case of heart failure and ischemia, there is stimulation of both sides.

In certain embodiments, control switch 1808 can be configured to control delivery of audio signals to earpieces 1802, 1804. Earpieces 1802, 1804 can include audio transducers 1806 for converting the audio signals into sound waves. The audio signal can be provided from audio processing/amplifier circuit 1814. Audio processing circuit 1814 can receive the audio signal from a locally stored file or from an external audio source connected to the device through interface 1816.

Control switch 1808 can be configured with hardware circuitry that allows for selective delivery of electrical stimulation to one or both earpieces 1802, 1804. Stimulation generator 1812 produces electrical signals for providing stimulation through one or more electrodes of one or more of earpieces 1802, 1804. For instance, the stimulation generator can be configured to produce an oscillating electrical signal at a particular frequency. The delivery of this oscillating signal to earpieces 1802, 1804 can then be selectively controlled using the control switch 1808. Control logic (e.g., a hardware processor circuit) 1810 can make a decision regarding how and when the oscillating signals are provided. Control logic 1810 can then generate control signals that indicate how the control switch 1808 should operate.

Interface 1816 can receive and transmit information from external components and devices. For instance, a sensor interface 1818 can receive data from one or more sensors, such as ECG 1822, block oxygenation sensor 1824 and pulse sensor 1826. These sensors are non-limiting examples. Information from these sensors can then be provided to control logic 1810 and used for a variety of purposes including selection of a stimulation profile and/or generation of a response surface. Interface 1816 can also be configured to allow for connection to remote devices 1828 for uploading treatment and sensor information and/or for updating/controlling of control logic 1810. In certain embodiments, the connection to remote devices 1828 can be accomplished using external (upload) interface 1820. The interface 1816 can be implemented using wired or wireless communications. The wireless communications can include, as non-limiting examples, Bluetooth, wireless local area network (WLAN) communications, near-field communications and others. Moreover, the sensor interface 1818 and the external (upload) interface 1820 can share a common communication circuit or can be implemented as separate communication circuit(s).

Figure 18B:
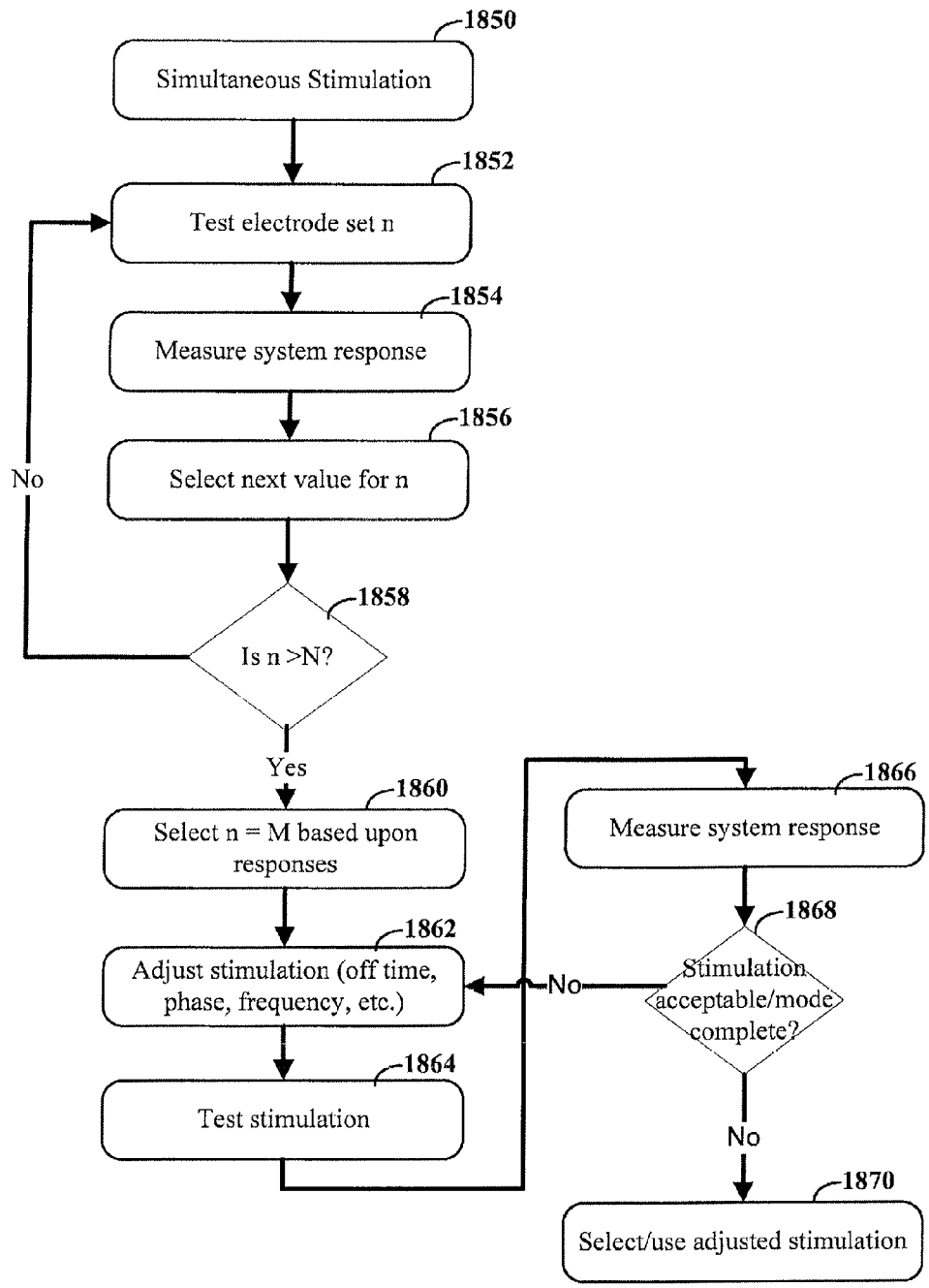
FIG. 18B shows a flow diagram for automated selection/detection of a pulse/stimulation profile for use with right and left auricular nerve stimulation; consistent with embodiments of the present disclosure.

FIG. 18B shows a flow diagram for automated selection/detection of a pulse/stimulation profile for use with right and left auricular nerve stimulation; consistent with embodiments of the present disclosure. Block 1850 represents that stimulation can provided to each ear at the same time. The stimulation is provided to a particular set of electrodes indicated by the variable "n." A number of "N" different sets of electrodes possibilities can be tested during the process. Each electrode set can specify one or more electrodes for either or both of the left and right earpieces. For instance, each electrode for each earpiece can be assigned a numerical number. A first electrode set (n=1) can correspond to electrode "1" in both earpieces. A second electrode set (n=2) can correspond to electrode "1" in the right earpieces and to both electrodes "1" and "2" in the left earpiece. Various other combinations are possible for the different sets "n."

The currently selected electrode set "n" is tested at block 1852. The system response (e.g., the patient's physiological responses) can be measured at block 1854 and for the tested electrode set "n." At block 1856, the system can select the next electrode set and modify "n" accordingly. In a particular non-limiting example, the system can be configured to increment the value of "n" until all "N" sets have been tested. Accordingly, the blocks 1852-1858 can be repeated until "n>N" as depicted by block 1858. In other embodiments, block 1858 can check for a satisfactory measurement from block 1854 and exit the blocks upon confirmation that a sufficient system response has been achieved. Still other embodiments allow for different selection algorithms for sets "n" and/or for test of block 1858.

Block 1860 allows for "n" to be set to a value "M." The value of "M" can be determined by comparing the measurements from block 1854 and selecting a set value that corresponds to an acceptable system response. Consistent with certain, optional embodiments, additional testing and configuration can be carried out. For instance, parameters for the stimulation waveforms can be adjusted at block 1862. A particular parameter can be the off-time between stimulation cycles. This can be particularly useful for mitigating issues with over stimulation of the nervous system and/or diminishing effectiveness stemming from such stimulation. For instance, it has been discovered that, in some instances, the effectiveness of stimulation can be reduced for continuous stimulation. It has also been discovered that switching stimulation off for a period of time (e.g., every few seconds) can be useful for mitigating such a reduction in effectiveness. Accordingly, the off time can be varied to allow for recovery of the neurotransmitters. On time can also be varied in certain embodiments.

The selected/adjusted stimulation profile can be tested at block 1864 and then the resulting system response can be measured at block 1866. Block 1868 represents a test to consider whether the current stimulation is acceptable and/or whether the testing mode should be completed. If not, the testing can be repeated with an adjusted/different stimulation profile. If so, then a stimulation profile can be selected from the test results as shown by block 1870.

Experimental results have found that 15 seconds on and 15 seconds off with a pulse of 20 Hz repetition frequency and 200 microseconds of pulse duration can be particularly effective. Other results suggest that 30 seconds on 30 seconds off is also effective. Additional variations are also contemplated.

The flow diagram of FIG. 18B, and variations thereof, can be particularly useful for providing treatment where there are limited resources for customizing treatments for a patient. For instance, during emergency situations, there can be limited time and expertise. Accordingly, the flow diagram can be automated to allow use in an emergency. For instance, an emergence medical technician (EMT) that is responding to a possible infarct can place auricular stimulators in the ears of a patient at risk. This can be done immediately upon contact with the patient, even before the patient has been positively diagnosed. In another instance, auricular stimulators can be provided upon admission to an emergency room, e.g., when there are signs of acute diastolic or systolic heart failure.

Experimental research suggests that bilaterally stimulation of the auricular nerve can reduce the infarct size by 80% when the auricular stimulation is started at the time of the infarct. Moreover, it is believed that the ischemic protection provided by auricular nerve stimulation occurs at the mitochondrial level inside the cells and thus it will provide protection for the microischemic events that are common in the progression of heart failure and during their acute episodes.

Figure 19A:
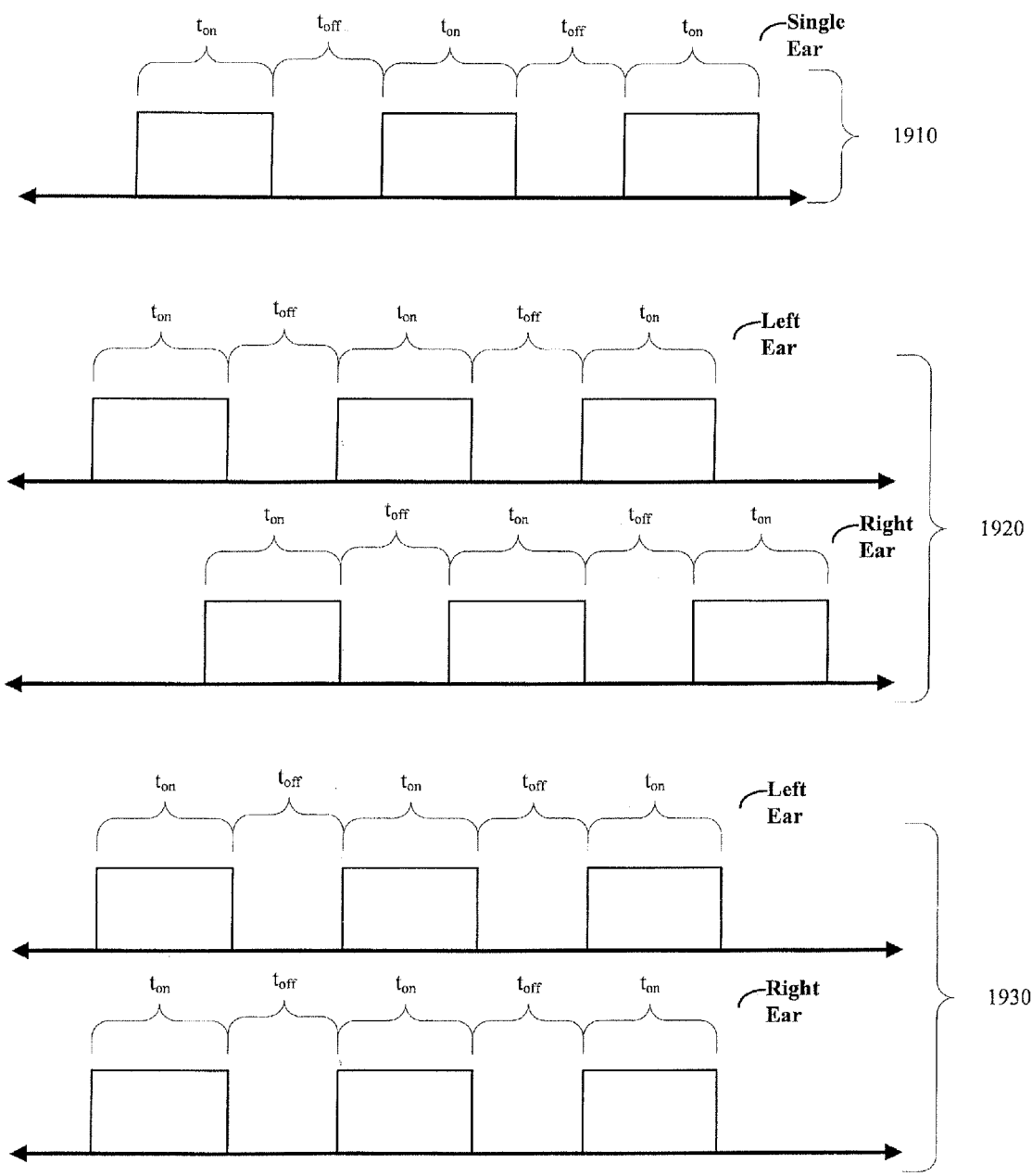
FIG. 19A shows example timing diagrams of the stimulation of only one or more auricular nerves, consistent with embodiments of the present disclosure.

FIG. 19A shows example timing diagrams of the stimulation of only one or more auricular nerves, consistent with embodiments of the present disclosure. FIG. 19A shows multiple waveforms 1910, 1920 and 1930 that each correspond to different stimulation profiles. Each waveform is depicted with reference to left and/or right earpieces, although the left and right distinction can be considered relatively arbitrary for most purposes. The different waveforms can be used and selected based upon, among other factors, the disease being treated, patient-specific parameters and from measured responses/feedback from testing of the different waveforms.

Waveform 1910 shows stimulation for a single ear in which stimulation on times alternate with stimulation off times. The length of the on times and off times are represented by $t_{on}$ and $t_{off}$, respectively. During the on time, stimulation can be provided at a particular frequency. For instance, a stimulation of around 20 Hz can be provided with pulse durations of around 200 μs. Various other frequencies and pulse durations are also possible. Moreover, these variables can vary during the on times, for certain embodiments. Although not necessarily limited thereto, experimental results suggest that embodiments can benefit from on times and off times that range from about 5 seconds to about 30 seconds.

Waveform 1920 includes on and off times for each (right and left) ear. The stimulations are provided in an alternating manner to each ear. In some embodiments, the on time of the right and off times for each ear can be set to the same value, although ratio between the on and off times can be changed. For instance, the on time for both right and left ears can be set to 15 seconds, while the off time for both ears can be set to 20 seconds. In this instance, there would be a 5 seconds each period during which stimulation would not be provided to either ear. By varying the ratio between on and off times, the on times for each ear can overlap, immediately follow one another or have a gap or delay between one another.

In certain embodiments, the on and off times can be separately modified for each ear. In one implementation, the total on and off time can be held common between the two ears. This allows the phase relationship to remain consistent by keeping the period/frequency of on-off cycles the same for both ears. In some embodiments, the total on-off time can be set different for each ear. This can result in a shifting phase relationship between the stimulation of each ear.

Waveform 1930 shows an example of embodiments in which the left and right ears are simultaneously stimulated. Consistent with the discussion of waveforms 1910 and 192, there are a number of different variations for on and off times and for corresponding embodiments.

Figure 19B:
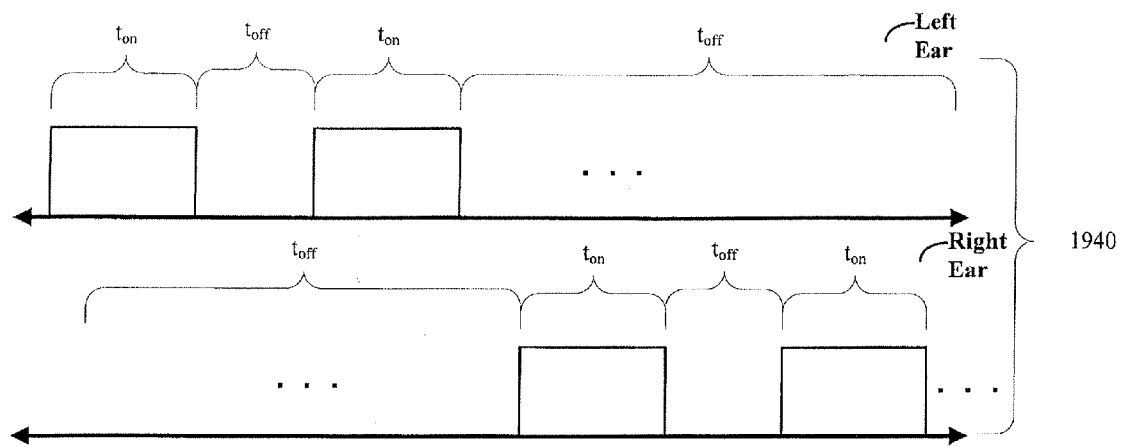
FIG. 19B shows example timing diagrams of the stimulation of only one or more auricular nerves, consistent with embodiments of the present disclosure.
Figure 19B:
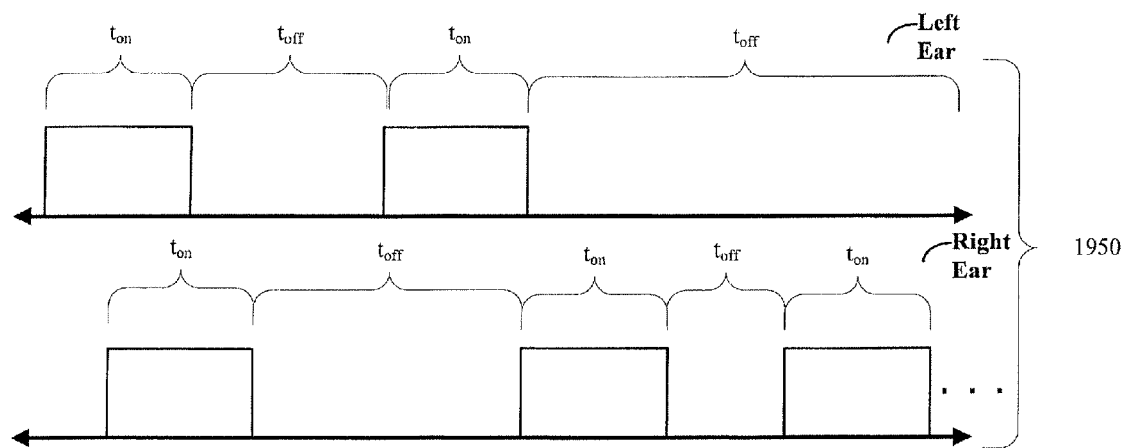

FIG. 19B shows example timing diagrams of the stimulation of only one or more auricular nerves, consistent with embodiments of the present disclosure. Waveform 1940 depicts embodiments where a period of on-off cycling is provided first for one ear and then for a second ear. For instance, stimulus for the left ear could be provided, for a minute or more, using on-off times of 15 seconds each. During this first time period, no stimulus is provided to the right ear. Thereafter, stimulus for the right ear could be provided, for a minute or more, using on-off times of 15 seconds each. During this second time period, no stimulus is provided to the left ear. Such alternating may allow for further recuperation of the nervous system for each side by providing an extended period of no stimulation.

Waveform 1950 depicts embodiments in which the off times (and/or on times) are randomly (or pseudo randomly) changed for one or both ears. In this manner, a regular pattern can be avoided, which may help to allow for the nervous system to recover. In certain instances, the random delay time can be weighted so that the times are distributed about a desired off time. For instance, the desired off time could be 15 seconds and random off-times could be selected using a distribution (e.g., standard distribution) centered around 15 seconds.

The various embodiments as discussed herein may be implemented using a variety of structures and related operations/functions. For instance, one or more embodiments as described herein may be computer-implemented or computer-assisted, by being coded as software within a coding system as memory-based codes or instructions executed by a logic circuit, computer processor or microprocessor. Such computer-based implementations are implemented using one or more programmable or programmed circuits that include at least one computer-processor and internal/external memory and/or registers for data retention and access. One or more embodiments may also be implemented in various other forms of hardware, such as a state machine, programmed into a circuit such as a field-programmable gate array, or implemented using electronic circuits such as digital or analog circuits. In addition, various embodiments may be implemented using a tangible storage medium that stores instructions which, when executed by a processor, perform one or more of the steps, algorithms, methods or processes described herein. These applications and embodiments may also be used in combination; for instance, certain functions can be implemented using discrete logic circuitry and discrete circuit components (e.g., digital circuit components) that generates an output that is provided as an input to a processor. For instance, received data can be processed using a combination of logic circuitry and a processing circuit configured using firmware or other software.

While the present disclosure has been described with reference to several particular example embodiments, those skilled in the art will recognize that many changes, including those discussed in the preceding paragraph, may be made thereto without departing from the spirit and scope of the present disclosure.

What is claimed is:

1. A method of auricular stimulation, comprising the steps of:

analyzing using a software data regarding anatomic points of an ear of a subject and determining using the software a stimulation location on the subject's ear based on the analysis;

generating a desired response surface for the subject, comprising:

obtaining one or more earpieces, each of the earpieces comprising a stimulation electrode and being associated with mathematically and statistically modeled outcomes of providing stimulation through that earpiece to an ear having one of a plurality of anatomical patterns;

selecting a desired change to an initial state of the subject;

determining anatomical parameters of the subject's ear;

identifying those of the outcomes modeled for the anatomical patterns matching the anatomical parameters of the subject's ear; and comparing the desired change to the initial state of the subject with the identified outcomes and determining the desired response surface based on the identified outcome that matches the desired change;

selecting the earpiece associated with the desired response surface for delivering stimulation to the subject;

positioning the stimulation electrode of the selected earpiece in the stimulation location;

delivering through a stimulation device a series of electrical stimulation signals to the stimulation electrode of the selected earpiece according to a stimulation profile; and adjusting the stimulation profile, comprising the steps of:

obtaining by the stimulation device feedback to the stimulation signals;

revising the desired response surface based on the feedback and performing an evaluation of the revised response surface against a threshold indicative of the effectiveness of mitigation of inflammatory disease processes;

adjusting the stimulation profile based on the evaluation of the revised response surface; and providing the adjusted stimulation profile for a delivery of electrical stimulation signals to the stimulation electrode.

2. The method of claim 1, wherein the effectiveness of stimulation of an auricular branch includes the effectiveness of hypertension treatment due to modulating activity of the parasympathetic system of the subject, and in response to the step of adjusting the stimulation profile, delivering another series of electrical stimulation signals to the stimulation electrode.

3. The method of claim 1, wherein the step of adjusting the stimulation profile includes increasing an amplitude of the electrical stimulation signals until the subject experiences discomfort, and further includes a step of decreasing amplitude of the electrical stimulation signals until the discomfort ceases.

4. The method of claim 1, wherein the step of positioning the earpiece further includes placing additional stimulation electrodes in three anatomic points of the subject's ear;
- activating the stimulation electrodes in sequence; and
- measuring physiological changes that are produced by each of the stimulation electrodes.

5. The method of claim 1, further comprising a step of forming one or more of the earpieces from a cast of an ear of the subject.

6. The method of claim 1, further including a step of applying a conductive gel to the stimulating electrode and to a reference electrode, and a step of measuring the impedance therebetween and adjusting the stimulation profile until the impedance value is inside an established range.

7. The method of claim 1, further comprising:
- identifying features of the subject comprising at least one of pathological features, physiological characteristics, and anatomical characteristics of the subject; and
- determining the desired response surface further based on at least one of the identified features.

8. The method of claim 1, further comprising:
- evaluating one or more changes to the initial state of the subject during the delivery of the electrical stimulation and signals; and
- modifying the stimulation profile based on the evaluated changes.

9. The method of claim 1, further comprising one or more of:
- using the earpiece to provide audio information in a form of air pressure waves to restore normal hearing;
- using an audio amplifier in the earpiece as a hearing aid;
- using an audio channel in the earpiece to receive audio from one or more electronic devices and to channel the received audio from the earpiece; and
- using the earpiece to provide audio for music therapy.

* * * * *